United States Patent
Crouther et al.

(10) Patent No.: US 11,832,973 B2
(45) Date of Patent: *Dec. 5, 2023

(54) METHODS FOR ANALYTE MONITORING MANAGEMENT AND ANALYTE MEASUREMENT DATA MANAGEMENT, AND ARTICLES OF MANUFACTURE RELATED THERETO

(71) Applicant: ABBOTT DIABETES CARE INC., Alameda, CA (US)

(72) Inventors: Nathan C. Crouther, San Francisco, CA (US); Timothy C. Dunn, San Francisco, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 215 days.

This patent is subject to a terminal disclaimer.

(21) Appl. No.: 17/170,991

(22) Filed: Feb. 9, 2021

(65) Prior Publication Data

US 2021/0161438 A1    Jun. 3, 2021

Related U.S. Application Data

(63) Continuation of application No. 15/475,094, filed on Mar. 30, 2017, now Pat. No. 10,945,646, which is a
(Continued)

(51) Int. Cl.
*A61B 5/145* (2006.01)
*A61B 5/00* (2006.01)
*G16H 40/63* (2018.01)

(52) U.S. Cl.
CPC ........ *A61B 5/7282* (2013.01); *A61B 5/14532* (2013.01); *A61B 5/14546* (2013.01); *A61B 5/742* (2013.01); *G16H 40/63* (2018.01)

(58) Field of Classification Search
None
See application file for complete search history.

(56) References Cited

U.S. PATENT DOCUMENTS 4,545,382 A    10/1985    Higgins et al.
4,711,245 A    12/1987    Higgins et al.
(Continued)

FOREIGN PATENT DOCUMENTS

WO    WO    12/2012
PCT/US2012/057608

OTHER PUBLICATIONS

Shahar, Y., et al., "Knowledge-Based Temporal Abstraction in Clinical Domains", 1996, retrieved from http://bmir.stanford.edu/file_assetlindex.php/413/BMIR-1995-0561.pdf, pp. 1-45.

*Primary Examiner* — Meredith Weare
(74) *Attorney, Agent, or Firm* — ONE LLP

(57) ABSTRACT

Generally, methods of analyte monitoring management, and articles of manufacturing related thereto, are provided. The methods include receiving analyte measurement data and analyzing the analyte measurement data for health related parameters. Recommendations are determined for creating or modifying a treatment program based on the analysis, and provided within a user-interface that enables a user to create or modify the treatment program. Further, generally, methods of for managing analyte measurement data, and articles of manufacturing related thereto, are provided. The methods include receiving analyte measurement data that represent data collected over a time period, and analyzing the analyte measurement data for analyte episodes within that time period. Threshold based episodes and/or rate-of-change based episodes may be determined.

9 Claims, 30 Drawing Sheets

Related U.S. Application Data continuation of application No. 13/629,262, filed on Sep. 27, 2012, now Pat. No. 9,622,689.

(60) Provisional application No. 61/540,332, filed on Sep. 28, 2011.

(56) References Cited

U.S. PATENT DOCUMENTS

| | | |
|---|---|---|
| 5,262,035 A | 11/1993 | Gregg et al. |
| 5,262,305 A | 11/1993 | Heller et al. |
| 5,264,104 A | 11/1993 | Gregg et al. |
| 5,320,725 A | 6/1994 | Gregg et al. |
| 5,356,249 A | 10/1994 | Heller et al. |
| 5,509,410 A | 4/1996 | Hill et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 6,071,391 A | 6/2000 | Gotoh et al. |
| 6,120,676 A | 9/2000 | Heller et al. |
| 6,121,009 A | 9/2000 | Heller et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,942,518 B2 | 9/2005 | Liamos et al. |
| 7,041,468 B2 | 5/2006 | Drucker et al. |
| 7,167,818 B2 | 1/2007 | Brown |
| 7,299,082 B2 | 11/2007 | Feldman et al. |
| 7,785,313 B2 | 8/2010 | Mastrototaro |
| 7,941,200 B2 | 5/2011 | Weinert et al. |
| 8,251,904 B2 | 8/2012 | Zivitz et al. |
| 8,688,386 B2 | 4/2014 | Shadforth et al. |
| 9,135,402 B2 | 9/2015 | Mensinger et al. |
| 9,622,689 B2 | 4/2017 | Crouther et al. |
| 10,945,646 B2 * | 3/2021 | Crouther ............ A61B 5/14546 |
| 2002/0177764 A1 | 11/2002 | Sohrab |
| 2004/0186365 A1 | 9/2004 | Jin et al. |
| 2006/0025662 A1 | 2/2006 | Buse et al. |
| 2006/0091006 A1 | 5/2006 | Wang et al. |
| 2006/0276771 A1 | 12/2006 | Galley et al. |
| 2007/0066873 A1 | 3/2007 | Kamath et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0128682 A1 | 6/2007 | Rosman et al. |
| 2007/0179434 A1 | 8/2007 | Weinert et al. |
| 2007/0199818 A1 | 8/2007 | Petyt et al. |
| 2008/0066305 A1 | 3/2008 | Wang et al. |
| 2008/0102441 A1 | 5/2008 | Chen et al. |
| 2008/0148873 A1 | 6/2008 | Wang |
| 2008/0267823 A1 | 10/2008 | Wang et al. |
| 2008/0300534 A1 | 12/2008 | Blomquist |
| 2008/0312841 A1 * | 12/2008 | Hayter ................ A61B 5/002 702/19 |
| 2010/0198034 A1 | 8/2010 | Thomas et al. |
| 2010/0218132 A1 | 8/2010 | Soni et al. |
| 2010/0256047 A1 | 10/2010 | Sieh et al. |
| 2010/0291604 A1 | 11/2010 | Rosman et al. |
| 2010/0299075 A1 | 11/2010 | Li et al. |
| 2010/0324401 A1 | 12/2010 | Otto et al. |
| 2010/0325868 A1 | 12/2010 | Wang et al. |
| 2010/0326842 A1 | 12/2010 | Mazza et al. |
| 2010/0332142 A1 | 12/2010 | Shadforth et al. |
| 2011/0004085 A1 | 1/2011 | Mensinger et al. |
| 2011/0130666 A1 | 6/2011 | Dong et al. |
| 2011/0184653 A1 | 7/2011 | Ray et al. |
| 2011/0193704 A1 | 8/2011 | Harper et al. |
| 2011/0245634 A1 * | 10/2011 | Ray ..................... A61B 5/1486 600/309 |
| 2012/0078067 A1 | 3/2012 | Kovatchev et al. |
| 2014/0088393 A1 | 3/2014 | Bernstein et al. |

\* cited by examiner

Confirm Patient and Therapy

Patient: Demo_T1, First C.   DOB: 01/01/1950   MRN: Demo_T1   Last Visit: 08/26/2011

Patient

Name: Demo_T1, First C.  Diagnosis: Type 1 Diabetes Mellitus
MRN: Demo_T1  Last Visit: 08/26/2011
Name: 01/01/1950

[Patient Not Correct]

Therapy since last visit

Treatment: T1 Basal Ins. + All Meal Bolus Ins.
Medications:

| Drug Name | Total Drug Dose | Units | Time Period |
|---|---|---|---|
| Glargine | 25 | unit | BT |
| Aspart | 8 | unit | AM |
| Aspart | 10 | unit | MD |
| Aspart | 12 | unit | PM |

[Edit Therapy]

[Confirm Patient and Therapy]

FIG. 12

View/Adjust Hypoglycemia Tolerance

Target Hypoglycemia Tolerance

Notes: Choose an appropriate hypoglycemia tolerance for your patient, balancing the trade-offs of more intensive targets with the possibility of increased risk of hypoglycemia. If a new target is selected, a new therapy recommendation will be calculated and the target will be set as the default for this patient for future analyses.

○ Low     A Low hypoglycemia tolerance may be appropriate for hypo unaware patients. The estimated frequency of hypoglycemic episodes is 1 per month.

⦿ Medium     A Medium hypoglycemia tolerance may be appropriate for most patients. The estimated frequency of hypoglycemic episodes is 2 per month.

○ High     A High hypoglycemia tolerance may be appropriate for some patients skilled at responding to low glucose or is using real-time continuous glucose monitoring with low glucose alarms. The estimated frequency of hypoglycemic episodes is 4 per month.

[Apply new target and run analysis again]     [Cancel]

FIG. 14

View/Adjust Hypoglycemia Tolerance

Target Glucose Median

○ 126 mg/dL, A1C = 6.0%
○ 140 mg/dL, A1C = 6.5%
● 154 mg/dL, A1C = 7.0%
○ 169 mg/dL, A1C = 7.5%
○ 183 mg/dL, A1C = 8.0%
○ 197 mg/dL, A1C = 8.5%

Notes: Choose an appropriate target median glucose for your patient, balancing the trade-offs of more intensive targets with the possibility of increased risk of hypoglycemia. If a new target is selected, a new therapy recommendation will be calculated and the target will be set as the default for this patient for future analyses.

| A1C% | eAGmg/dL |
|---|---|
| 5 | 97 |
| 5.5 | 111 |
| 6 | 126 |
| 6.5 | 140 |
| 7 | 154 |
| 7.5 | 169 |
| 8 | 183 |
| 8.5 | 197 |
| 9 | 212 |
| 9.5 | 226 |
| 10 | 240 |
| 10.5 | 255 |
| 11 | 269 |
| 11.5 | 283 |
| 12 | 298 |

[Apply new target and run analysis again]

[Cancel]

resolve Hypoglycemia Risk.

FIG. 15

Review Guidance & Modify Therapy

Patient: Last, First MI  DOB: Feb 22, 1970  MRN: dgd0226  Last Visit: Mmm DD, YYYY

[Review New Therapy >]

BG Analysis    Guidance

+ BG Variability (click to expand guidance)

+ Medication Adjustment

| Fasting<br>Above Target<br>High Variability | Glucose levels are high during fasting. However, high BG<br>hypoglycemia risk. Consider the following actions:<br>○ 1. Reduce variability, no LA dose adjustment (More)<br>○ 2. Decrease LA dose, if variability cannot be reduced |

First priority should be to take steps to reduce glucose variability during fasting. If it is unlikely that variability can be reduced substantially, consider the next option. — A13

| Post-Dinner<br>Above Target<br>High Variability | Glucose levels are high after dinner. However, high BG<br>hypoglycemia risk. Consider the following actions:<br>○ 1. Reduce variability, no RA dinner dose adjustment<br>○ 2. Decrease RA dinner dose, if variability cannot be reduced (More) |

If it is not likely that variability during fasting can be reduced, consider decreasing LA dose to reduce hypoglycemia risk. Note that this may also raise glucose levels after meals. — A13

| Post-Lunch<br>Above Target<br>High Variability | Glucose levels are high after lunch. However, high BG<br>hypoglycemia risk. Consider the following actions:<br>○ 1. Reduce variability, no RA lunch dose adjustment<br>○ 2. Decrease RA lunch dose, if variability cannot be reduced (More) |

| Post-Breakfast<br>Above Target<br>Low Hypo Risk | Glucose levels are high after breakfast. Consider the following action:<br>○ 1. Increase RA breakfast dose (More) |

SDM Quick Guide: Type 1: Insulin Adjustment Guidelines

[Copy Previous Therapy to New]

Review Therapy

Patient: Demo_T1, First C.
Medical Record No.: Demo_T1
Date of Birth: 01/01/1950
Last Visit: 08/26/2011

Today's Visit Date:
Aug. 28 2011

| Patient Therapy | Patient Instructions | HCP Notes |

New Therapy       [Edit]

New Treatment:
T1 Basal Ins. + All Meal Bolus Ins.

New Medications:

| Drug Name | Total Drug Dose | Units | Time Period |
|---|---|---|---|
| Glargine | 25 | unit | BT |
| Aspart | 8 | unit | AM |
| Aspart | 10 | unit | MID |
| Aspart | 12 | unit | PM |

[ Copy Previous Therapy to New ]

Previous Therapy

Treatment:
T1 Basal Ins. + All Meal Bolus Ins.

Medications:

| Drug Name | Total Drug Dose | Units | Time Period |
|---|---|---|---|
| Glargine | 25 | unit | BT |
| Aspart | 8 | unit | AM |
| Aspart | 10 | unit | MID |
| Aspart | 12 | unit | PM |

[ Therapy Entry Complete > ]

FIG. 25

Configure Meter - 08/26/2011

Patient: Demo_T1, First C.  DOB: 01/01/1950  MRN: Demo_T1  Last Visit: 08/28/2011

Save To Meter >

Typical Meal Times

Breakfast: 8:00AM   Lunch: 12:00PM   Dinner: 6:00PM   (Adjust)

SMBG Reminder Schedules (select one)

○ 5 checks per day for 7 days — (35 total) This schedule is adequate for observing glycemic patterns, however there can be some monitoring uncertainty, and is typically most appropriate for patients with a low risk for hypoglycemia.

○ 8 checks per day for 7 days — (56 total) This schedule is more effective at assessing glycemic patterns after meals, is typically most appropriate for patients with a low or moderate risk for hypoglycemia.

○ 5 checks per day for 14 days — (70 total) This schedule is effective at assessing glycemia patterns, and typically has high monitoring certainty. It is typically most appropriate for patients with a moderate or high risk for hypoglycemia.

○ 8 checks per day for 14 days — (112 total) This schedule is effective at assessing glycemic patterns with high certainty. It is typically most appropriate for patients with a moderate or high risk for hypoglycemia.

○ None

NOTE: By selecting this option, no analysis or guidance will be provided at the next visit.

Select when to begin SMBG reminders:

Start Date: [ 8/27/2011 ▼ ]   End Date: 08/27/2011   (Earliest next visit date)

FIG. 26

Configure Meter - 08/26/2011

Patient: Demo_T1, First C. DOB: 01/01/1950 MRN: Demo_T1 Last Visit: 08/26/2011

[ Print Orders > ]

Print the following summary materials:

☒ Print HCP Order
☒ Print Patient Order

Print the following diabetes self-care patient education materials:
<u>Select All</u>

<u>Preview</u> ☐ Medication dose compliance and correct doses
<u>Preview</u> ☐ Treating low glucose
<u>Preview</u> ☐ Food: Importance of consistency in food intake and food choices
<u>Preview</u> ☐ Introduction to Carb Counting
<u>Preview</u> ☐ Healthy snacking
<u>Preview</u> ☐ Alcohol and glucose
<u>Preview</u> ☐ Exercise and glucose
<u>Preview</u> ☐ Illness and glucose

[ Close Record (no printing) ]

METHODS FOR ANALYTE MONITORING MANAGEMENT AND ANALYTE MEASUREMENT DATA MANAGEMENT, AND ARTICLES OF MANUFACTURE RELATED THERETO

CROSS-REFERENCE TO RELATED APPLICATIONS

This application is a continuation of U.S. application Ser. No. 15/475,094, filed Mar. 30, 2017, which is a continuation of U.S. application Ser. No. 13/629,262, filed Sep. 27, 2012, now U.S. Pat. No. 9,622,689, which claims priority to U.S. Provisional Application No. 61/540,332, filed Sep. 28, 2011, the disclosures of all of which are incorporated by reference herein in their entireties for all purposes.

INTRODUCTION

Diabetes patients regularly consult with their health care practitioner (HCP) in order to assess the progress of their diabetes management, and to evaluate areas in need for improvement. The patient's responsibilities may include keeping diligent record of relevant information such as meal times and amount, fasting periods, insulin intake, exercise, and glucose measurements.

When patients return for a visit to the HCP, the HCP may collect the glucose measurements and acquire information from the collection of measurements. Information acquired from the measurements by existing software typically focus on overall summary statistics, such as median and percent or measurements in a target range. The software provides a general picture of the glucose measurements as a whole and does not focus in on more specific episodes within the measurements that may be useful in treatment determination or modification. Such general summary information is limited and more clinically meaningful health related information is lacking.

SUMMARY

In some aspects of the present disclosure, methods for analyte monitoring management are provided. The methods include receiving analyte measurement data and analyzing the analyte measurement data for health related parameters. The analyte measurement data represents analyte measurement data collected over a time period. The methods also include determining recommendations for creating or modifying a treatment program based on the analysis. The recommendations modulate the health related parameters to improve one or more of the health related parameters. The methods include generating a user-interface to enable a user to create or modify the treatment program. The user interface provides the recommendations to guide the user in creating or modifying the treatment program. The recommendations are optional and not required to be implemented by the user. The methods also include configuring an analyte monitoring device according to the created or modified treatment program. In some aspects of the present disclosure, articles of manufacture are provided that include a machine-readable medium having machine-executable instructions stored thereon for analyte monitoring management according to the methods described above.

In some aspects of the present disclosure, methods for managing analyte measurement data are provided. The methods include receiving analyte measurement data that represent data collected over a time period, and analyzing the analyte measurement data for analyte episodes within that time period. The analyte episodes include at least one threshold based episode. The threshold based episode is based on measurements meeting an entrance threshold for entering the threshold based episode. Further, the threshold based episode requires at least one of: a minimum number of measurements meeting the entrance threshold; a minimum duration of time meeting the entrance threshold; and a minimum area for measurements meeting the entrance threshold. The methods also include storing the analyte episodes in memory. In some aspects of the present disclosure, articles of manufacture are provided that include a machine-readable medium having machine-executable instructions stored thereon for managing analyte measurement data according to the methods described above.

In some aspects of the present disclosure, methods for managing analyte measurement data are provided. The methods include receiving analyte measurement data that represent data collected over a time period, and analyzing the analyte measurement data for analyte episodes within that time period. The analyte episodes include at least one rate-of-change based episode. The rate-of-change based episode requires a core of the episode to meet a threshold rate for a duration threshold. The methods also include storing the analyte episodes in memory. In some aspects of the present disclosure, articles of manufacture are provided that include a machine-readable medium having machine-executable instructions stored thereon for managing analyte measurement data according to the methods described above.

INCORPORATION BY REFERENCE

The following patents, applications and/or publications are incorporated herein by reference for all purposes: U.S. Pat. Nos. 7,041,468; 5,356,786; 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; 5,264,014; 5,262,305; 5,320,715; 5,593,852; 6,746,582; 6,284,478; 7,299,082; U.S. Provisional Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. 2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. Patent Application Publication No. 2010/0198034; and U.S. Provisional Application No. 61/149,639 titled "Compact On-Body Physiological Monitoring Device and Methods Thereof", the disclosures of each of which are incorporated herein by reference in their entireties.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

FIGS. 10-30 illustrate the user interface that is generated to enable a user to create or modify a treatment program, and further provides the recommendations to guide the user in creating or modifying the treatment program.

DETAILED DESCRIPTION

Figure 1:
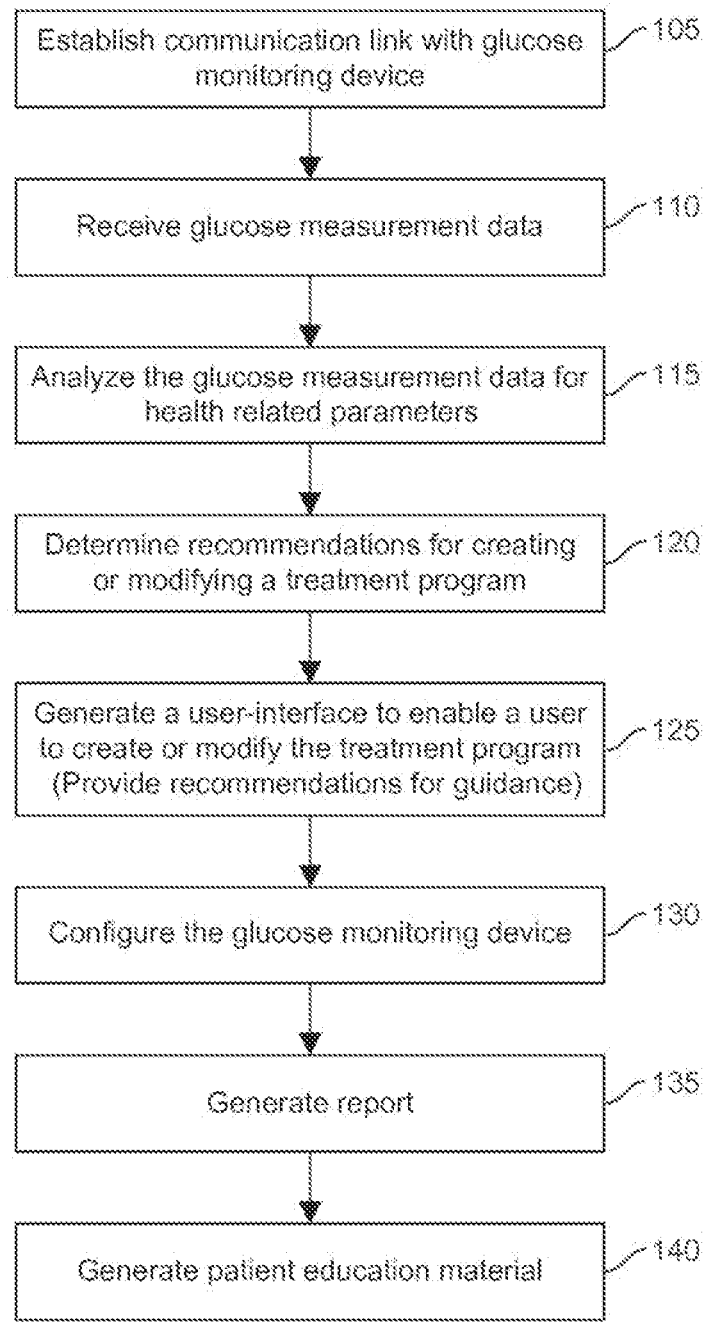
FIG. 1 illustrates a flowchart of a method for analyte (e.g., glucose) monitoring management, according to one embodiment.

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

In the description of the present disclosure herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the present disclosure. It will be understood that a corresponding description of these various terms applies to corresponding linguistic or grammatical variations or forms of these various terms. It will also be understood that the present disclosure is not limited to the terminology used herein, or the descriptions thereof, for the description of particular embodiments. Merely by way of example, the present disclosure is not limited to particular analytes, bodily or tissue fluids, blood or capillary blood, or sensor constructs or usages, unless implicitly or explicitly understood or stated otherwise, as such may vary. The publications discussed herein are provided solely for their disclosure prior to the filing date of the application. Nothing herein is to be construed as an admission that the embodiments of the present disclosure are not entitled to antedate such publication by virtue of prior invention. Further, the dates of publication provided may be different from the actual publication dates which may need to be independently confirmed.

As summarized above, in some aspects of the present disclosure, methods for analyte monitoring management are provided. The methods include receiving analyte measurement data and analyzing the analyte measurement data for health related parameters. The analyte measurement data represents analyte measurement data collected over a time period. The methods also include determining recommendations for creating or modifying a treatment program based on the analysis. The recommendations modulate the health related parameters to improve one or more of the health related parameters. The methods include generating a user-interface to enable a user to create or modify the treatment program. The user interface provides the recommendations to guide the user in creating or modifying the treatment program. The recommendations are optional and not required to be implemented by the user. The methods also include configuring an analyte monitoring device according to the created or modified treatment program. In some aspects of the present disclosure, articles of manufacture are provided that include a machine-readable medium having machine-executable instructions stored thereon for analyte monitoring management according to the methods described above.

FIGS. 10-30 illustrate and describe example methods for analyte monitoring management. Moreover, FIGS. 10-30 illustrate the user interface that is generated to enable a user to create or modify the treatment program, and further provides the recommendations to guide the user in creating or modifying the treatment program. The user interface also enables the configuring of an analyte monitoring device according to the created or modified treatment program, the importing of glucose measurement data, and the printing of orders including materials such as reports, summaries, educational material, instructional material, etc.

The user may be, for example, a physician or other health care practitioner, and the user-interface provided via a data processing device, such as a personal computer, a portable computer including a laptop or a handheld device (e.g., a personal digital assistant (PDA), a telephone including a cellular phone (e.g., a multimedia and Internet-enabled mobile phone including an iPhone™, a Blackberry®, or similar phone), etc.

In one embodiment, a communication link is established with an analyte (e.g., glucose) monitoring device. The glucose monitoring device may be connected (wired or wirelessly), for example, to the data processing device. For instance, a patient may use the glucose monitoring device between visits to a physician, or other health care practitioner, to collect glucose measurement data, and then have the glucose monitoring device connect either wired or wireless with the data processing device (e.g., computer, laptop, cellular phone, etc.) of the physician during the next visit.

The glucose measurements that are received represent data that has been collected over a time period. Various time periods may be used, such as two weeks, one month, two months, or any other time period. For example, the time period may reflect the time between visits. In the example provided, the glucose monitoring device is connected to the physician's computer and glucose measurement data and the glucose measurement data is received by the physician's computer from the glucose monitoring device. In one embodiment, the glucose measurement data may be received from other devices than the glucose monitoring device—e.g., another personal computer, portable computer, handheld device, or memory storage device, such as Flash memory stick, CD-ROM, etc.

The health related parameter may be, for example, a risk of hypoglycemia or hyperglycemia, deviation of median glucose with respect to a target range, a degree of glucose variability, or any other parameter or indicator of health or area of concern thereof. The risk level identifies a level of risk of hypoglycemia based on the collected measurement data. The level of risk of hypoglycemia or hyperglycemia may be established in various manners—e.g., by looking to hypoglycemic or hyperglycemic episodes, such as the number, duration, timing, or other characteristics thereof. Deviations of median glucose may be categorized, for example, as above, below, or within a target range. The degree of glucose variability indicates how variable the glucose measurements are. Widely varying glucose measurements may present difficulties in controlling treatment or parameters. For example, small variations in glucose measurements may facilitate more accurately estimating the proper dosage, or change in dosage, to improve or control blood glucose levels.

In some aspects, the analyzing of the analyte measurement data for health related parameters includes analyzing the measurement data for analyte episodes within the collection time period. In one embodiment, the episodes are derived according to the methods described herein relating to threshold based episodes. In one embodiment, the episodes are derived according to the methods described herein relating to rate-of-change based episodes. In one embodiment, the episodes are derived according to methods described herein relating to both the threshold based episodes and the rate-of-change based episodes.

The recommendations are provided to modulate the health related parameters to improve one or more of the health related parameters. For example, the recommendations may relate to lowering glucose variability, adjusting median glucose to be close to the target range, reducing a risk of hypoglycemia or hyperglycemia, etc. The recommendations are optional and are not required to be implemented by the user.

In one embodiment, a database stores recommendations and corresponding conditions that are associated with or required by the recommendations. For example, a table may include predetermined conditions that are associated with one or more recommendations. Based on the conditions that exist, the appropriate recommendation may be determined. In some instances, the conditions and requirements may take into account attributes of the episodes themselves—e.g., type of episode, specific combinations of episodes present, number of episodes, relation to event or activities (e.g., meals, fasting periods, exercise, medication administration, times of day (e.g., morning, afternoon, night, sleeping periods, etc.), etc. Based on the resulting attributes of episodes found for the measurement data, the associated recommendations in the database will be selected.

As stated above, the user-interface is generated to enable the user (e.g., physician or other health care practitioner) to create or modify treatment. It should be appreciated that the term "user-interface" is used broadly herein. The user interface may be visual and/or audio based. For example, the user interface may include a graphical user interface (GUI) generated for display on a display device. It should be appreciated that the user interface may be implemented as a program containing one or more GUIs and may include one or more application "screens" or "windows".

The generated user-interface provides the user with the necessary tool to modify or create a treatment program for the patient. However, the recommendations go further and guide the user in creating or modifying the treatment program such that the health related parameters may be modulated to improve the health related parameter. The recommendations may for instance, recommend or suggest that one or more health related parameters be targeted for improvement. Furthermore, the recommendations may recommend steps necessary to achieve such improvement.

Figure 13:
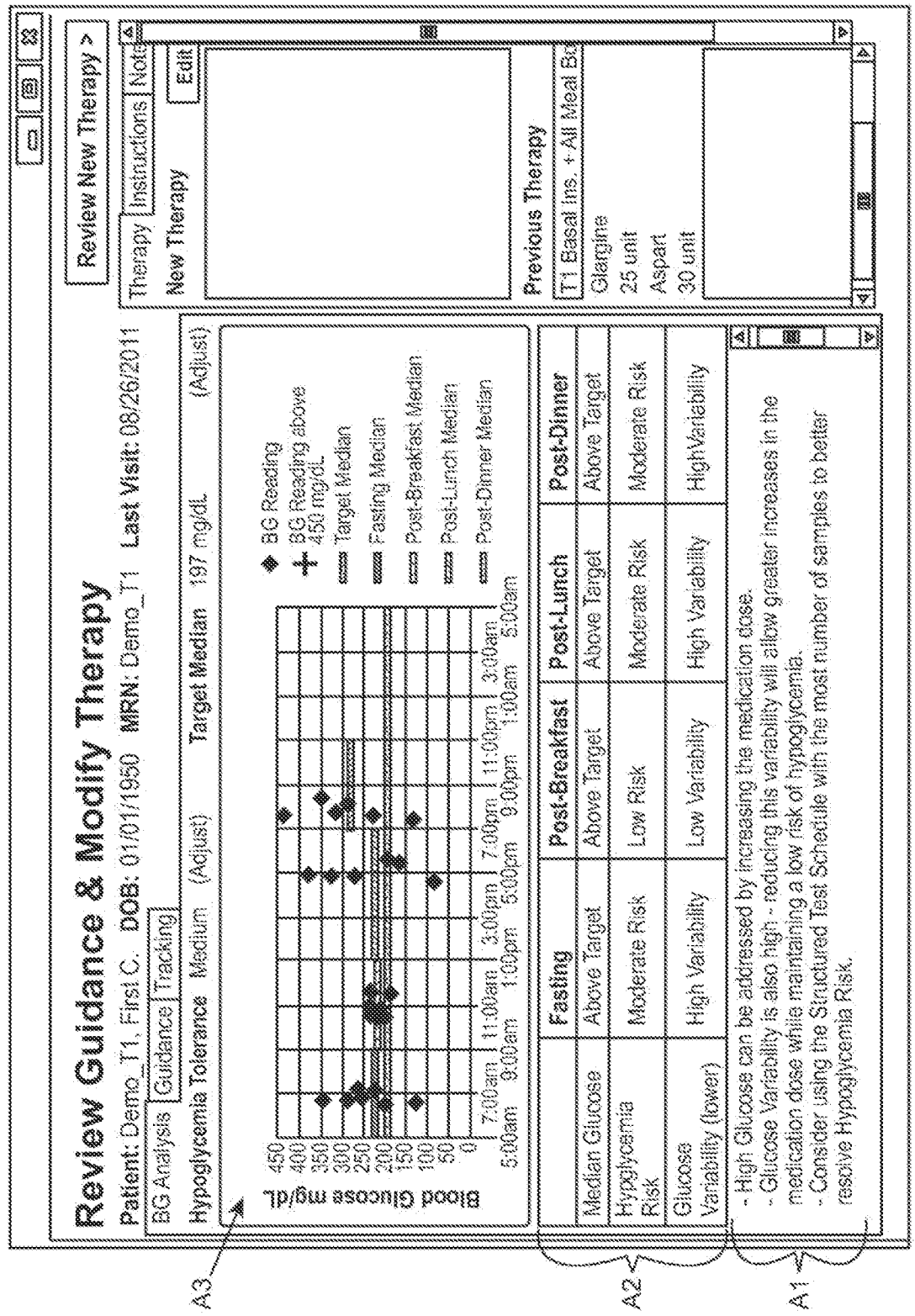
Figure 16:
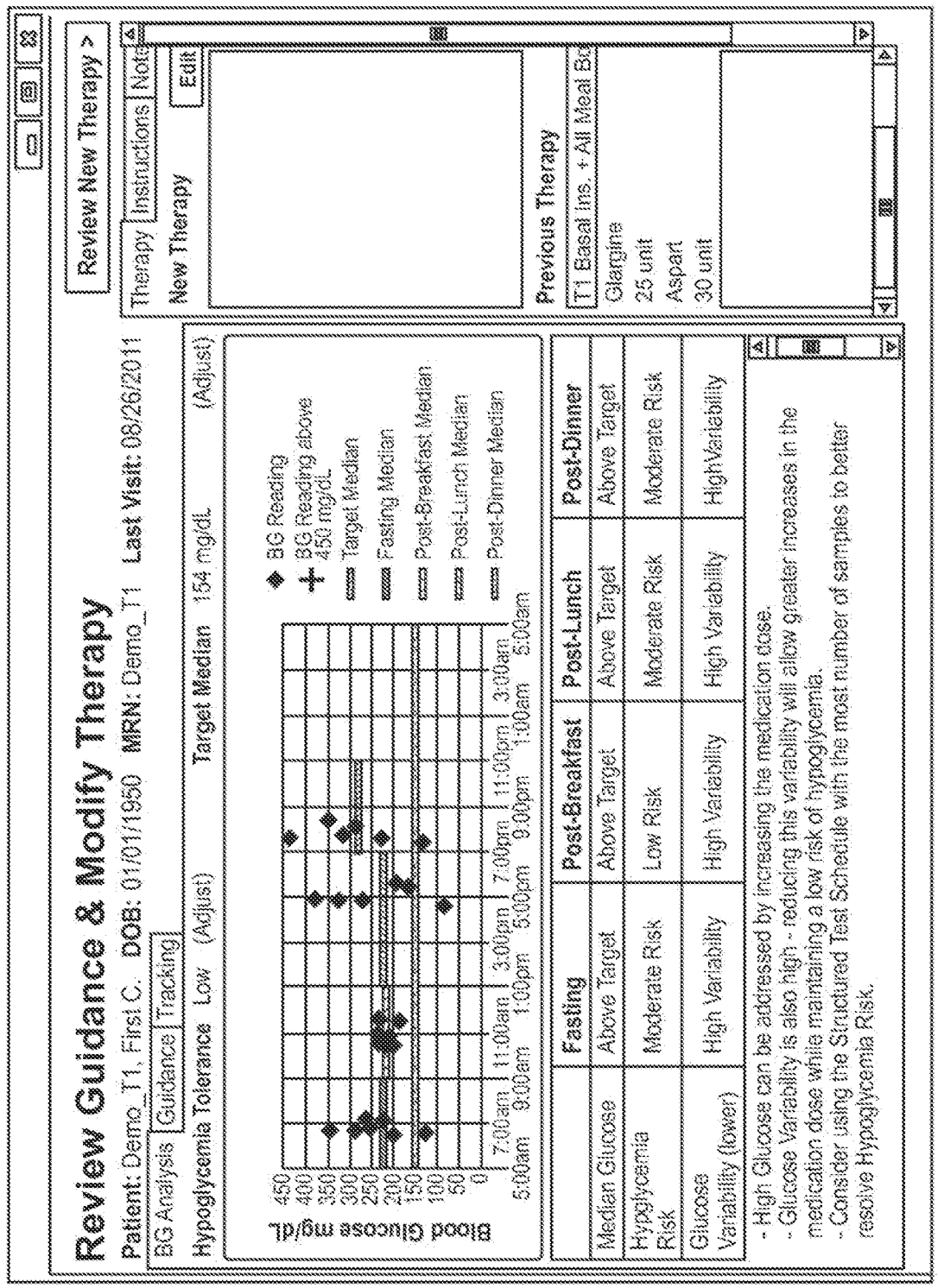

The recommendations may be implemented in a variety of manners within the user interface. For example, FIG. 13 illustrates an example GUI that includes recommendations resulting from analyzing glucose measurement data that was collected over a time period. The recommendations A1 are provided in summary format along with a summary of the health related parameters A2 for specific time periods in the day (e.g., during fasting periods, post-breakfast periods, post-lunch periods, and post-dinner periods). A summary A3 of the glucose measurement data over a 24-hour plot is also shown in the GUI.

In one embodiment, the recommendations include a recommendation for creating or modifying medication parameters of the treatment program. The medication parameters may include, for instance, the medication selected, the amount of dosage, the frequency or timing of administration, etc. For example, it may be determined that a risk of hypoglycemia is present (e.g., high risk) and recommended that medication (e.g., insulin) be increased. The recommendation may also note that glucose variability is high and that reducing this variability will allow for greater increases in the medication dose. The recommendation may further include recommended steps that can be taken to assist with the improvement, such as using a greater number of measurements to be scheduled for higher sample count, as shown. In one embodiment, the recommendation for creating or modifying medication parameters are provided for different time periods, including time periods centered around events such as fasting periods, meal times (e.g., during post-breakfast periods, post-lunch periods, post-dinner periods), exercise or other activities, etc.

Figure 17:
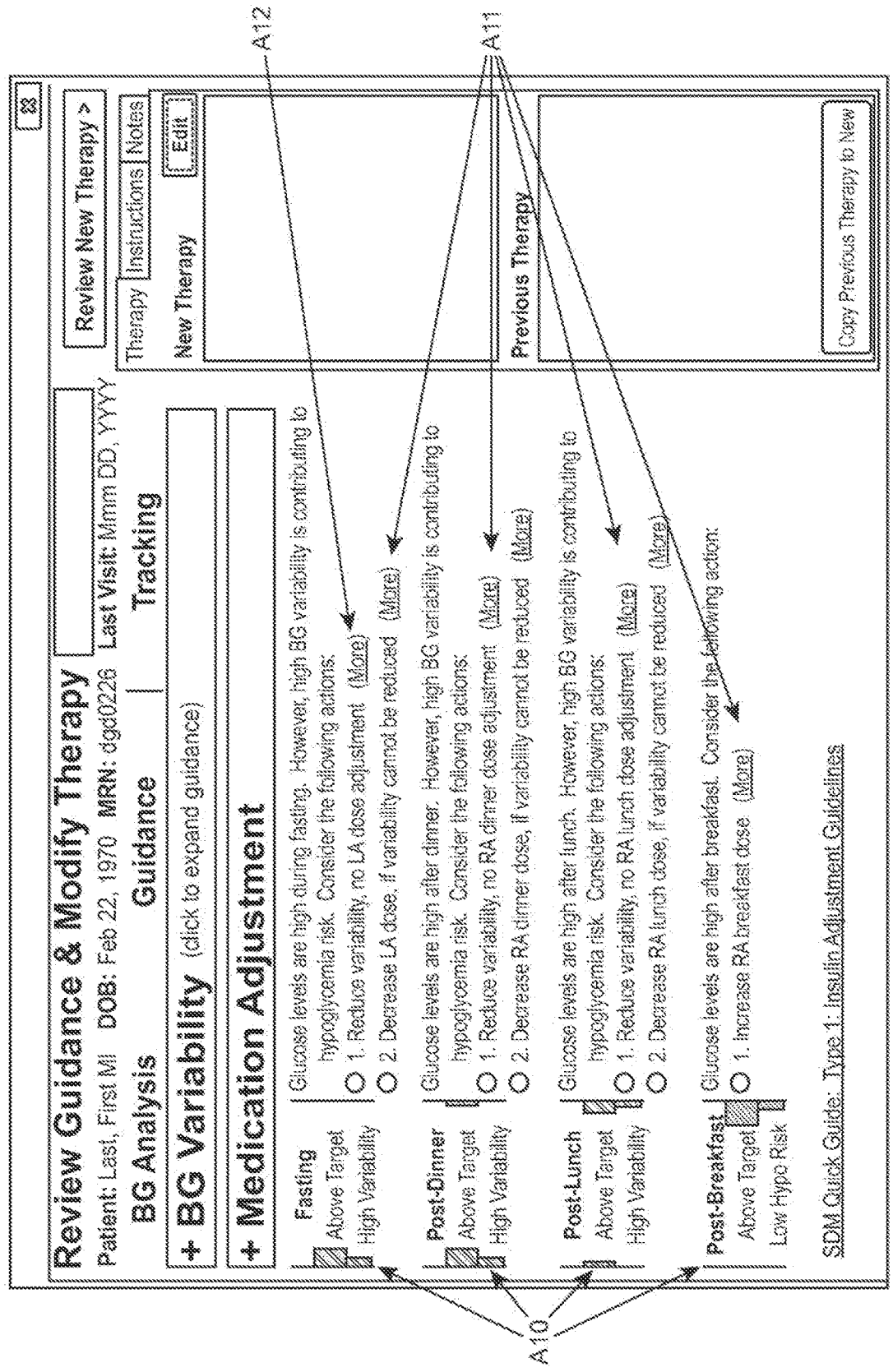
Figure 19:
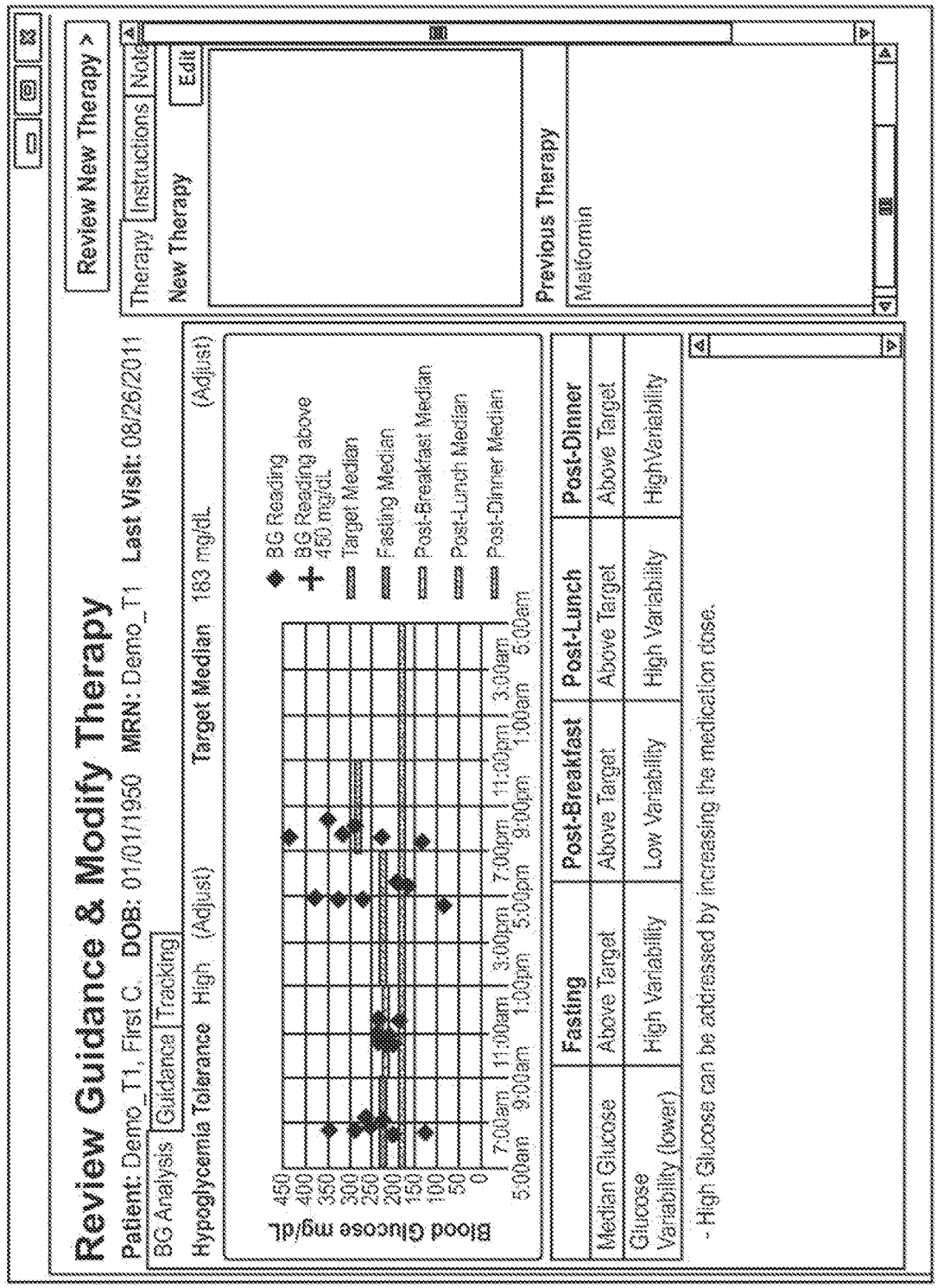

FIG. 17 illustrates recommendations provided along with the option for the user to select the corresponding course of action. In the example shown, the recommendations are provided for medication adjustment purposes. For instance, a summary A10 of the health related parameters are listed for different event periods—e.g., median glucose and glucose variability are provided fasting periods to indicate that these are the areas of concern determined for this period. The user interface provides the user with suggested or recommended courses of action A11. For example, as shown for fasting, the user is presented with the option of reducing variability with no medication dose adjustment; or the option of decreasing the medication adjustment if variability cannot be reduced. The user interface also provides the user with a trigger element A12 to get more information or further recommendation related thereto, as shown by pop up windows A13 on FIG. 18.

Figure 21:
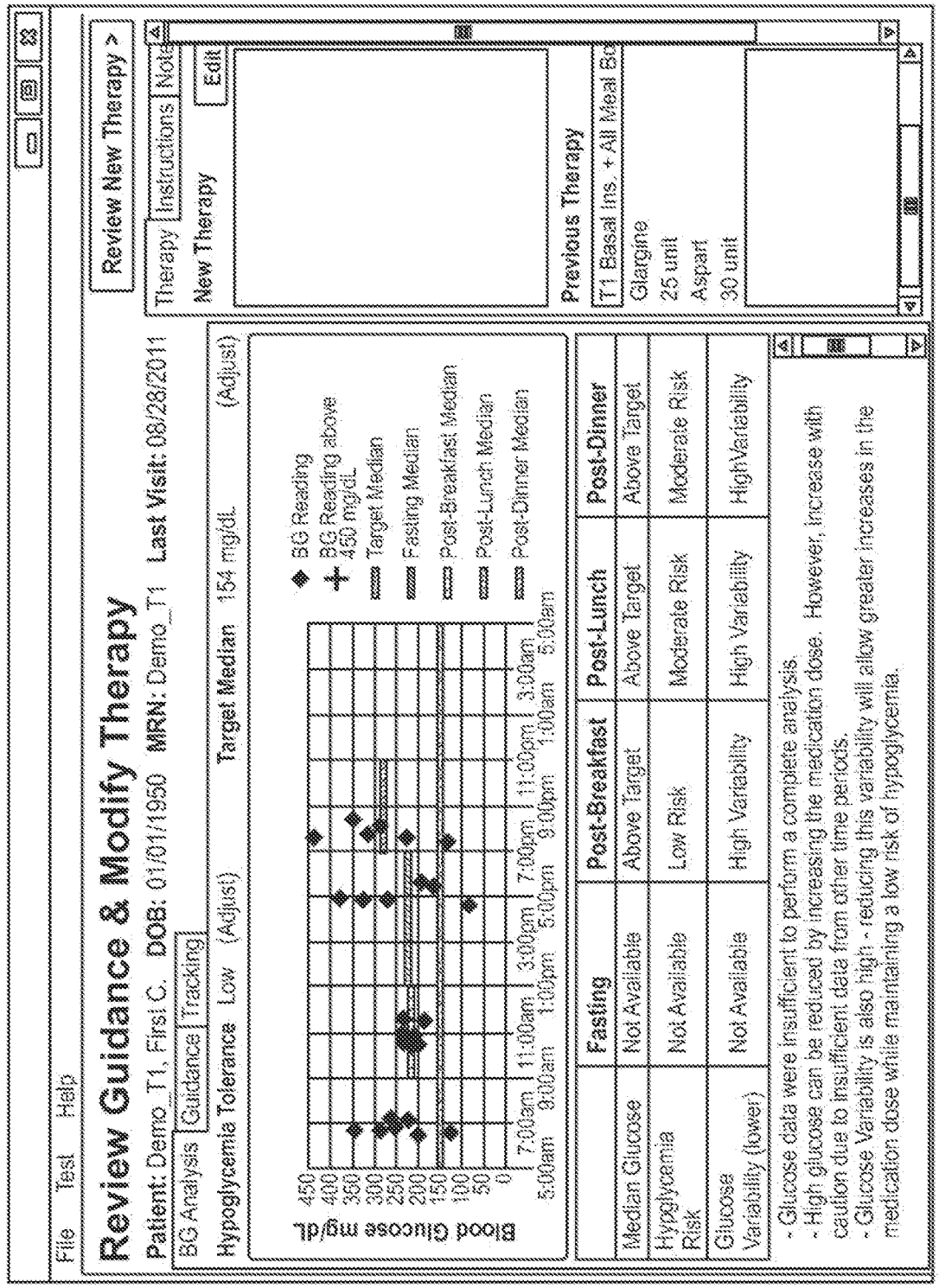
Figure 22:
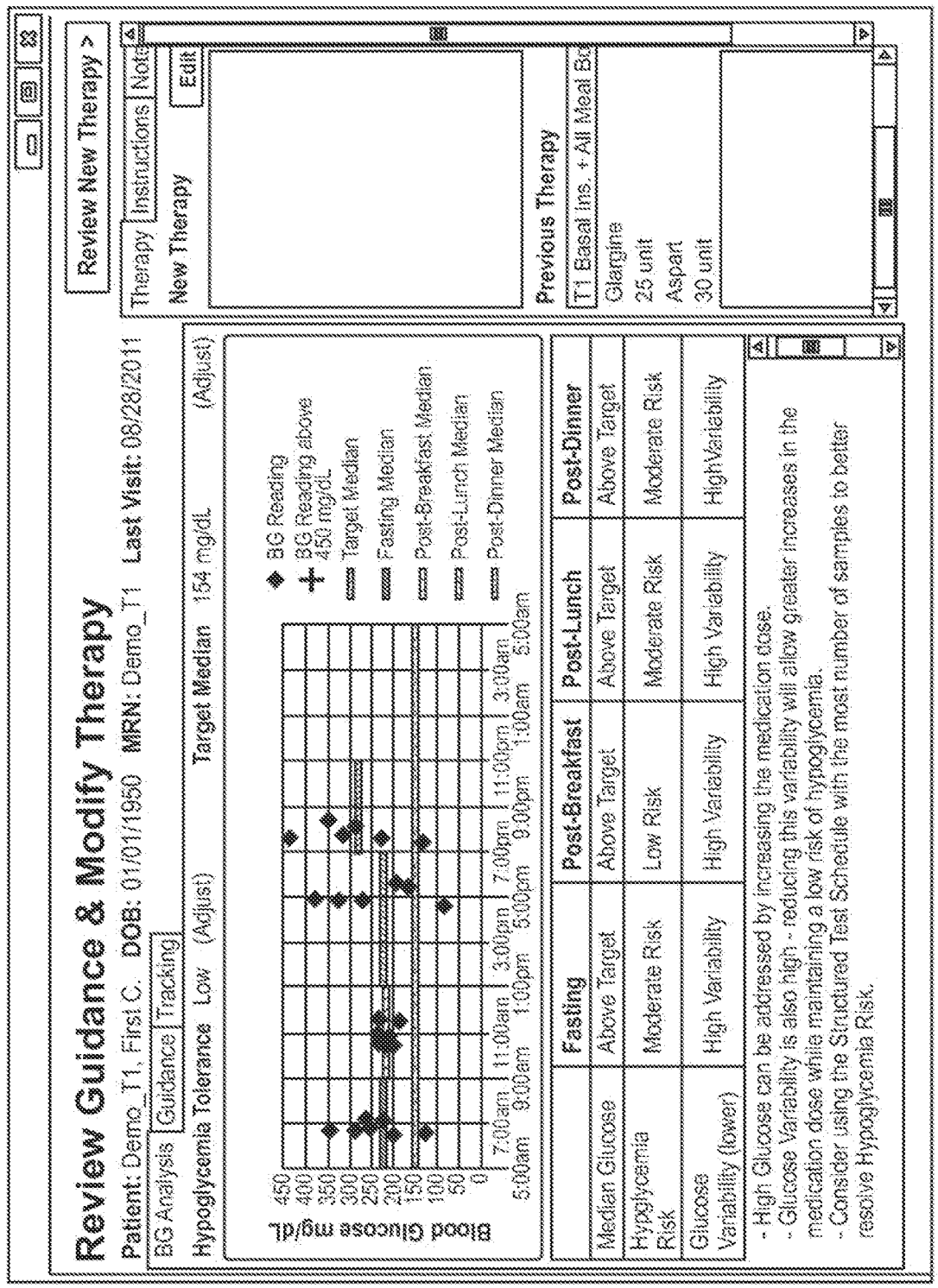
Figure 27:
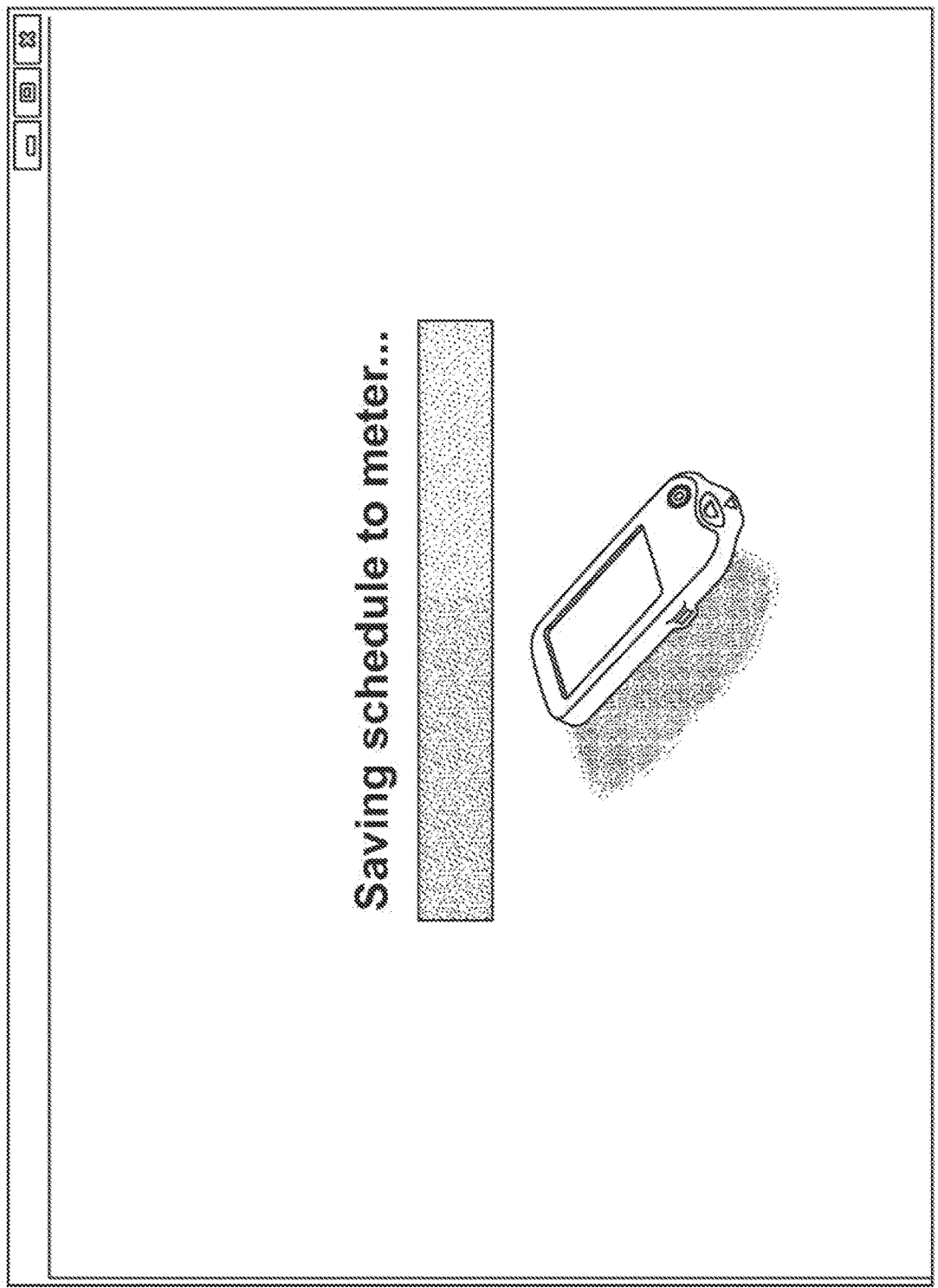
Figure 30:
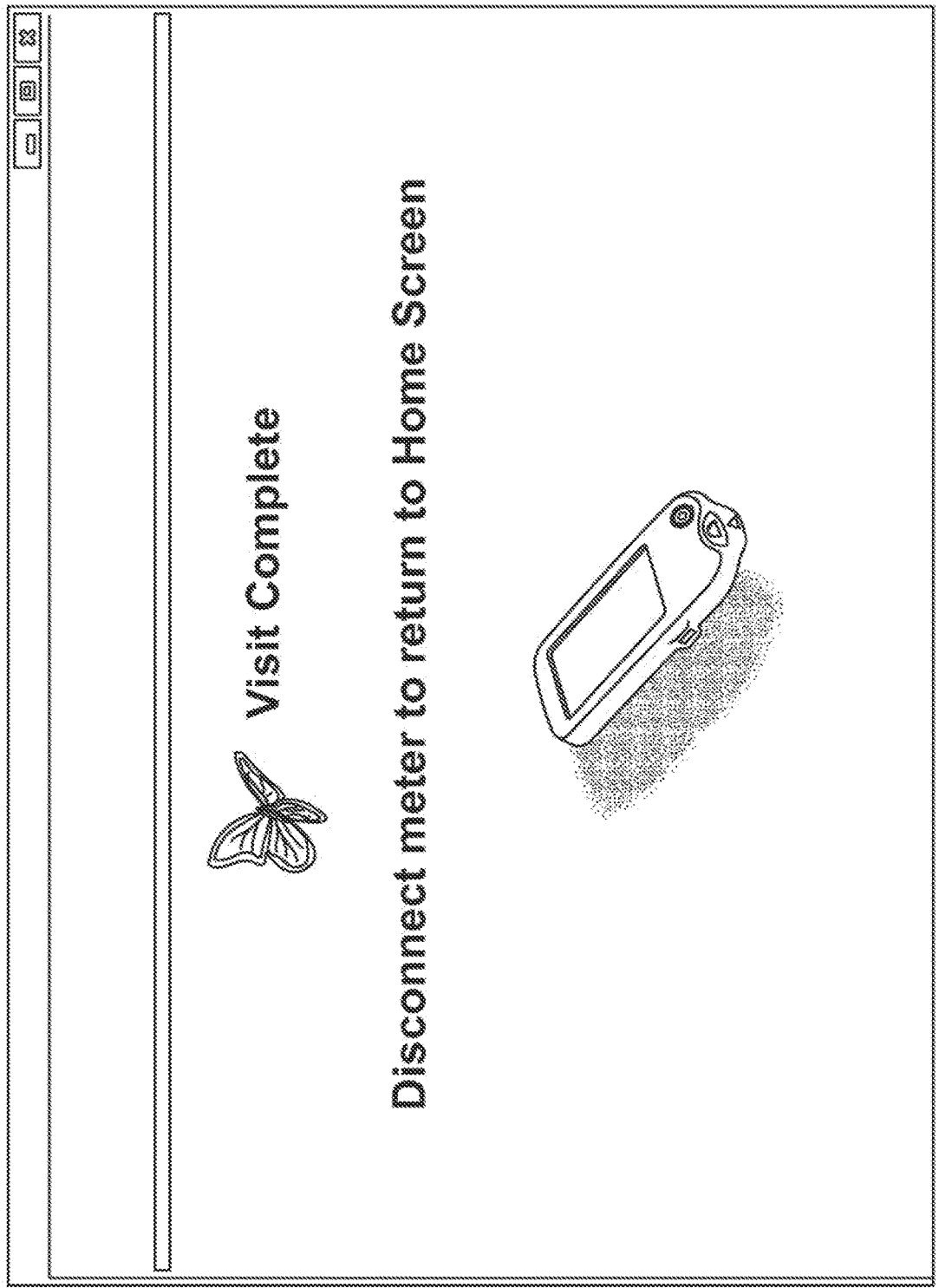

In one embodiment, insufficient measurement data is also accounted for and conveyed on the user interface. For example, FIG. 21 illustrates an example user-interface when insufficient data is encountered. As shown, the recommendation may state that that there is insufficient data to perform an analysis, and may present a warning or suggest a course of action to be taken with caution.

Figure 23:
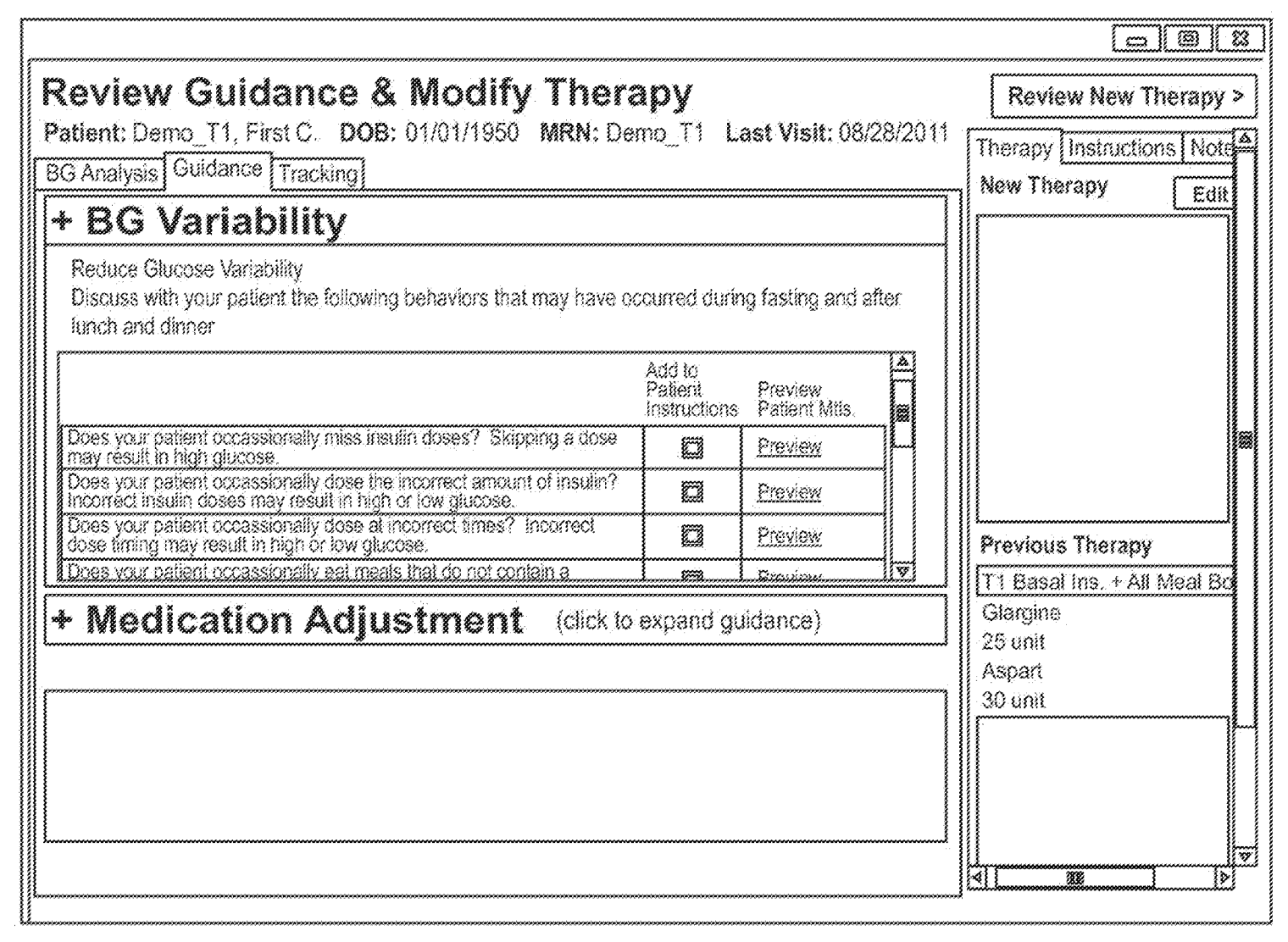
Figure 24:
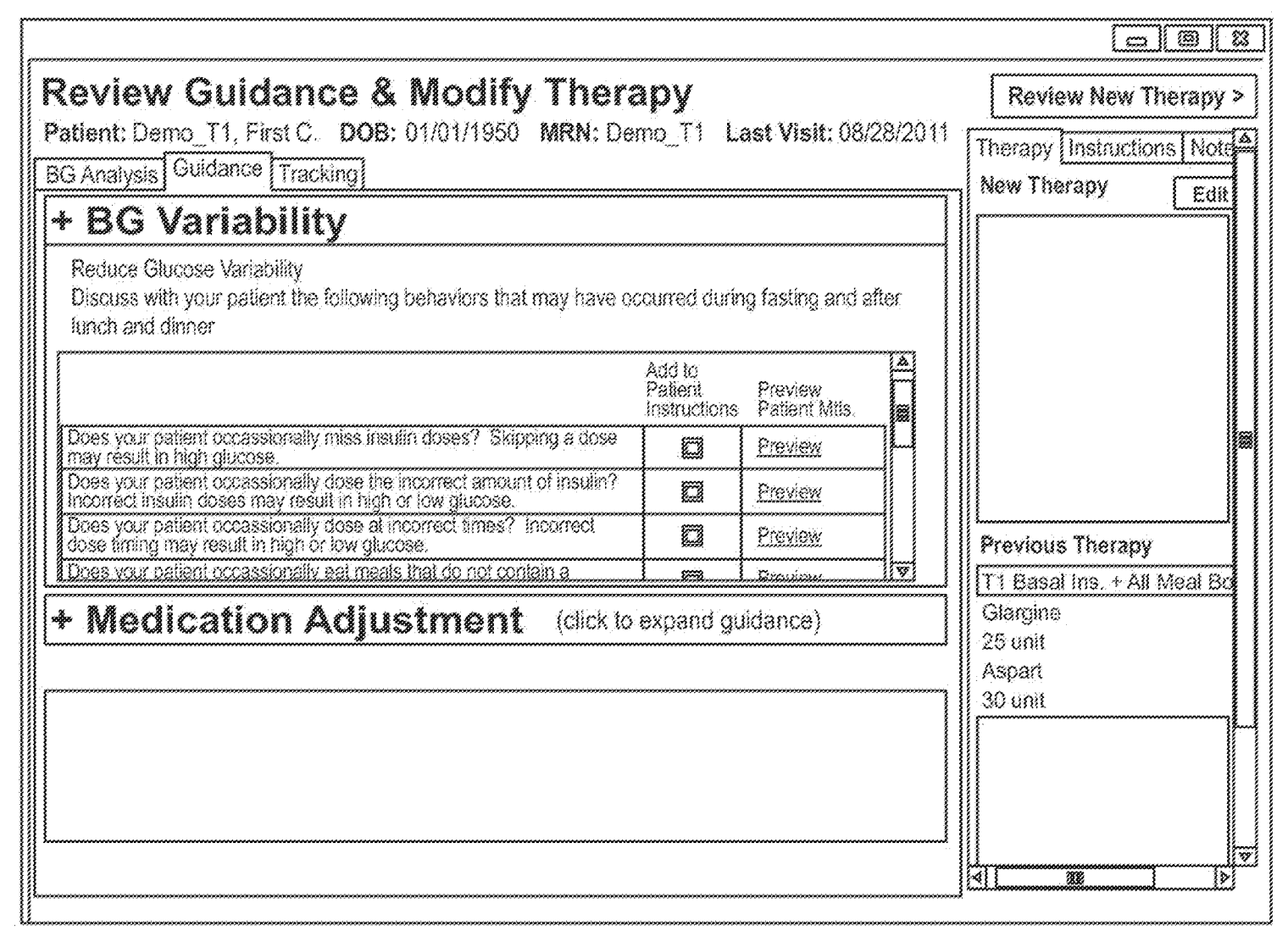

In one embodiment, glucose variability is a health related parameter in the analysis. The user interface may provide recommendations, for example, in the form of specific questions to ask the patient or to determine about the patient. For example, FIGS. 23-24 illustrate example questions to be answered by the user to assist with treatment creation or modification.

In one embodiment, educational material or other reference material may be provided to assist or remind the user of the subject matter related to the recommendation. For example, guidelines or flowcharts (e.g., medication administration guidelines) or other pertinent information (e.g., information regarding the medication, such as ingredients, side effects, recommended dosages, etc.) may be provided to assist the user with actions related to the recommendation. For instance, example educational information is shown on FIGS. 17, 18, and 20.

In one embodiment, the user interface enables the user to generate a structured schedule, including setting reminders related to the modified or created treatment program. For example, reminders to take measurement readings may be set and ultimately implemented in the glucose monitoring device to remind the patient (or user of the glucose monitoring device) to take a measurement at the appropriate time, to avoid missing measurements or taking them too infrequently. Thus, if the treatment program is modified to include a higher number of measurements to be taken, then the reminders may be set accordingly—e.g., to provide a reminder for every measurement reading. Other schedules and reminders may set, such as meal times, applicable start and end dates, etc.

As stated above, the glucose monitoring device is configured according to the created or modified treatment program. For example, the glucose monitoring device may be configured by programming the device with the created or modified reminder schedule. For instance, the reminder schedule may be transmitted to the to the glucose monitoring device from the physician's computer via the wired or wireless communication link. The configuration data may be stored in the glucose monitoring device and thereafter be implemented when the patient begins using the device again. It should be appreciated that many other configuration data may be included that relate to alerts, medication calculations, meter settings, event reminders, etc.

Furthermore, in one embodiment, a report is generated. Various reports may be generated to provide the physician and/or patient with related information. For example, reports may be generated and then printed. Example information that may be included in a report may include a summary of the glucose measurement data, health related parameters, recommendations, configuration settings, instructions, etc. In one embodiment, educational material may be generated and printed for the patient and/or physician. For instance, the educational material may include information on medication, instructions for treatment, self-care instructions, or educational material geared toward educating the patient. FIG. 28 illustrates some example material (e.g., summary materials and educational materials) that may be generated and provided to the patient.

It should be appreciated that the following embodiments described are exemplary and that other variations may be provided in other embodiments. It should be appreciated that one or more of the features described may be deleted, combined, etc., in other embodiments. Furthermore, while the following embodiments are described with respect to glucose, it should be appreciated that the concepts and principles apply to analytes in general, and that other analytes (e.g., ketone bodies) may apply in other embodiments.

FIG. 1 illustrates a flowchart of a method for analyte (e.g., glucose) monitoring management, according to one embodiment. At block 105, a communication link is established with an analyte (e.g., glucose) monitoring device. For instance, a patient may use the glucose monitoring device between visits to a physician, or other health care practitioner, to collect glucose measurement data, and then have the glucose monitoring device connect either wired or wireless with the computer of the physician during the next visit.

At block 110, glucose measurement data is received. The glucose measurement data includes data that has been collected over a time period. Various time periods may be used, such as two weeks, one month, two months, or any other time period. For example, the time period may reflect the time between visits. In the example provided, the glucose monitoring device is connected to the physician's computer and glucose measurement data and the glucose measurement data is received by the physician's computer from the glucose monitoring device.

At block 115, the glucose measurement data is analyzed for health related parameters. The health related parameter may be, for example, a risk of hypoglycemia or hyperglycemia, deviation of median glucose with respect to a target range, a degree of glucose variability, or any other parameter or indicator of health or area of concern thereof. The risk level identifies a level of risk of hypoglycemia based on the collected measurement data. The level of risk of hypoglycemia or hyperglycemia may be established in various manners—e.g., by looking to hypoglycemic or hyperglycemic episodes, such as the number, duration, timing, or other characteristics thereof. Deviations of median glucose may be categorized, for example, as above, below, or within a target range. The degree of glucose variability indicates how variable the glucose measurements are.

In one embodiment, the analyzing of the analyte measurement data for health related parameters includes analyzing the measurement data for analyte episodes within the collection time period. For instance, the episodes are derived according to the methods described later with respect to threshold-based episodes and rate-of-change based episodes.

Based on the analysis of the glucose measurement data in block 115, recommendations for creating modifying a treatment program are determined, as represented at block 120. The recommendations modulate the health related parameters to improve one or more of the health related parameters. For example, the recommendations may relate to lowering glucose variability, adjusting median glucose to be close to the target range, reducing a risk of hypoglycemia, etc. The recommendations are optional and are not required to be implemented by the user.

In one embodiment, a database stores recommendations and corresponding conditions that are associated with or required by the recommendations. For example, a table may include predetermined conditions that are associated with one or more recommendations. Based on the conditions that exist, the appropriate recommendation may be determined. In some instances, the conditions and requirements may take into account attributes of the episodes themselves—e.g., type of episode, specific combinations of episodes present, number of episodes, relation to event or activities (e.g., meals, fasting periods, exercise, medication administration, times of day (e.g., morning, afternoon, night, sleeping periods, etc.), etc. Based on the resulting attributes of episodes found for the measurement data, the associated recommendations in the database will be selected.

At block 125, a user-interface is generated to enable the user (e.g., physician or other health care practitioner) to create or modify treatment. For example, the user interface may include a graphical user interface (GUI) generated for display on a display device and includes one or more application "screens" or "windows".

The generated user-interface provides the user with the necessary tool to modify or create a treatment program for the patient. However, the recommendations go further and guide the user in creating or modifying the treatment program such that the health related parameters may be modulated to improve the health related parameter. The previous discussion and examples for recommendations apply here as well.

At block 130, the glucose monitoring device is configured according to the created or modified treatment program. For example, the glucose monitoring device may be configured by programming the device with the created or modified reminder schedule. For instance, the reminder schedule may be transmitted to the to the glucose monitoring device from the physician's computer via the wired or wireless communication link. The configuration data may be stored in the glucose monitoring device and thereafter be implemented when the patient begins using the device again.

At block 135, a report is generated. Various reports may be generated to provide the physician and/or patient with related information. For example, reports may be generated and then printed. At block 140, any patient education material is generated to be provided (e.g., printed or transferred to the glucose monitoring device) for viewing at a later time.

Threshold Based Episode

As summarized above, in some aspects of the present disclosure, methods for managing analyte measurement data are provided. The methods include receiving analyte measurement data that represent data collected over a time period, and analyzing the analyte measurement data for analyte episodes within that time period. The analyte episodes include at least one threshold based episode. The threshold based episode is based on measurements meeting an entrance threshold for entering the threshold based episode. Further, the threshold based episode requires at least one of: a minimum number of measurements meeting the entrance threshold; a minimum duration of time meeting the entrance threshold; and a minimum area for measurements meeting the entrance threshold. The methods also include storing the analyte episodes in memory. In some aspects of the present disclosure, articles of manufacture are provided that include a machine-readable medium having machine-executable instructions stored thereon for managing analyte measurement data according to the methods described above.

In practical applications, analyte measurement data may provide problems for episode detection due to various factors. For example, gaps in measurement data (e.g., missing measurements) may present problems in determining if the gap exists in one episode or exists between two episodes. Furthermore, outliers or other brief measurement data points may provide problems by improperly crossing value thresholds (e.g., entrance thresholds or exit thresholds) and rate of change based thresholds. Noise may present similar issues.

It should be appreciated that rate-of-change based thresholds refer to thresholds of rate-of-change (also referred to herein "rate thresholds" or "threshold rate"). The term "value thresholds" is used herein generally to distinguish the thresholds from thresholds for rate-of-changes. Such value thresholds may include, for example, entrance thresholds, exit thresholds, thresholds of duration (also referred to herein as "duration thresholds"), thresholds for minimum number of measurements, thresholds for minimum area, etc. Value thresholds may also be referred to herein simply as thresholds in some instances.

In some aspects, methods are provided that resolve the above-mentioned issues and problems in episode detection. For example, these methods may be used to search glucose measurement values to detect extreme episodes of clinical interest. Therefore, the episode may be more clinically meaningful. In addition, the present disclosure specifies the properties of episodes that can be clinically meaningful. These properties can also be used to construct sequences or "chains" of episodes that have specific clinical meaning related to self-care behaviors.

The core logic of episode analysis falls into two families: threshold based, and rate-of-change based thresholds. Looking for episodes in both directions, for example, suggests four basic episode types: low glucose/hypoglycemia (measurements below a threshold); high glucose/hyperglycemia (measurements above a threshold); glucose fall (rate-of-change more negative than a negative threshold rate); and glucose rise (rate-of-change more positive than a positive threshold rate). In one embodiment, a "within target" episode is defined to identify an episode where the measurements are maintained between an upper and lower bound for a period of time. Detection of these episodes can be done by extension of the threshold-based episode detection algorithms.

Grouping all consecutive measurements (e.g., above or below) a threshold to form an episode creates issues and challenges in practical applications. For example, very brief episodes or outlier values may skew the identification of episodes by being improperly identified as an episode.

In one embodiment, the methods for managing analyte measurement data described herein requires threshold based episodes to be based on measurements meeting an entrance threshold. Further, the threshold based episode requires one or more of the following: a minimum number of measurements meeting the entrance threshold; a minimum duration of time meeting the entrance threshold; and a minimum area for measurements meeting the entrance threshold. In one embodiment, all three criteria may be required. In one embodiment, all three are required to have an episode.

It should be appreciated that "meeting" a threshold is used herein to mean that the threshold is triggered. It should be appreciated that "meeting a threshold" is used generally herein to refer to instances where a threshold is triggered by values "equal to" or "exceeding" the threshold; as well as to other instances where a threshold is triggered by values only "exceeding" the threshold. Furthermore, it should be appreciated that the phrase "exceeding a threshold" is used herein generally to refer to values that are beyond the threshold such that the threshold is triggered, whether the threshold is triggered by measurements above the threshold (e.g., hyperglycemic episodes) or below the threshold value (hypoglycemic episodes). This applies to both value based thresholds and rate-of-change thresholds. For example, if a measurement is greater than a threshold for hyperglycemia, then the threshold is exceeded and the threshold is met. Similarly, if a measurement is less than a threshold for hypoglycemia, then the threshold is exceeded and the threshold is met.

Gaps in measurement data may also provide problems by significantly altering an episode duration. In one embodiment, a threshold based episode is defined based on a gap threshold such that a single episode is maintained at any gaps shorter than the gap threshold, and split into two separate potential episodes at any gaps meeting the gap threshold. The potential episodes are determined to be episodes if all other criteria are met.

Noise may also present problems in defining episodes, especially when the true value is near a threshold. For example, noise may cause many episodes to be recorded when the true value is close to the threshold. In one embodiment, a threshold based episode is defined based on an exit threshold for exiting the episode, such that the at least one threshold based episode ends when measurements meet the exit threshold. In one embodiment, the exit threshold is a value "outside" the entrance threshold. The term "outside" is used here to mean that the exit threshold does not "equal" the entrance threshold or "exceed" the entrance threshold such that it would trigger the entrance threshold. Therefore, to exit an episode, measurements within the episode must first reach and pass the entrance threshold before eventually reaching the exit threshold. In this way, measurement will be "debounced" such that the episode is only terminated following a threshold crossing if the signal also crosses the exit threshold.

Properties of threshold based episodes may be defined for clinical utility, including but not limited to: threshold value, most extreme value (magnitude of excursion past threshold), episode duration, or episode area. It should be appreciated that many other episode types may be provided, each of which, if independently clinically relevant, could form the basis for reports and analysis.

The following is an example pseudocode implementation of a threshold-based episode detection algorithm, according to one embodiment:

```
//"State" is the previous condition, "PointState" is the condition for the new point
void BuildList( )
{
    EpisodeState State = NotInEpisode;
    For Each CGMValue In Database
        EpisodeState PointState = GetEpisodeState (CGMValue);
        if (PointState == InEpisode)
        {
            if (Gap from previous point >= maximum gap)
            {
                //end of possible episode
                //if it passes all checks...
                        if (ReadingsInEpisode >= MinimumReadings
                            && EpisodeDuration >=
                            MinimumDuration &&
                            EpisodeArea >= MinimumArea)
                        {
                            //add it to the list of episodes
                        }
                //Start of possible episode
                //record start time, reset point count and cumulative area
            }
            if (State == NotInEpisode)
                //Start of possible episode
                    //record start time, reset point count and cumulative area
            }
            else if (State == InEpisode)
            {
                //continuation of possible episode
                //push back end time, increment point count, add to cumulative
                    area
            }
            else // if (State == BetweenThresholds)
            {
                //debounce region
            }
            State = InEpisode;
        }
        else if (PointState == NotInEpisode)
        {
            if (State == BetweenThresholds || State == InEpisode)
            {
                //end of possible episode
                //if it passes all checks...
                        if (ReadingsInEpisode >= MinimumReadings
                            && EpisodeDuration >=
                            MinimumDuration
                            && EpisodeArea >= MinimumArea)
                        {
                            //add it to the list of episodes
                        }
            }
            State == NotInEpisode;
        }
    Next CGMValue
}
```

Figure 2A:
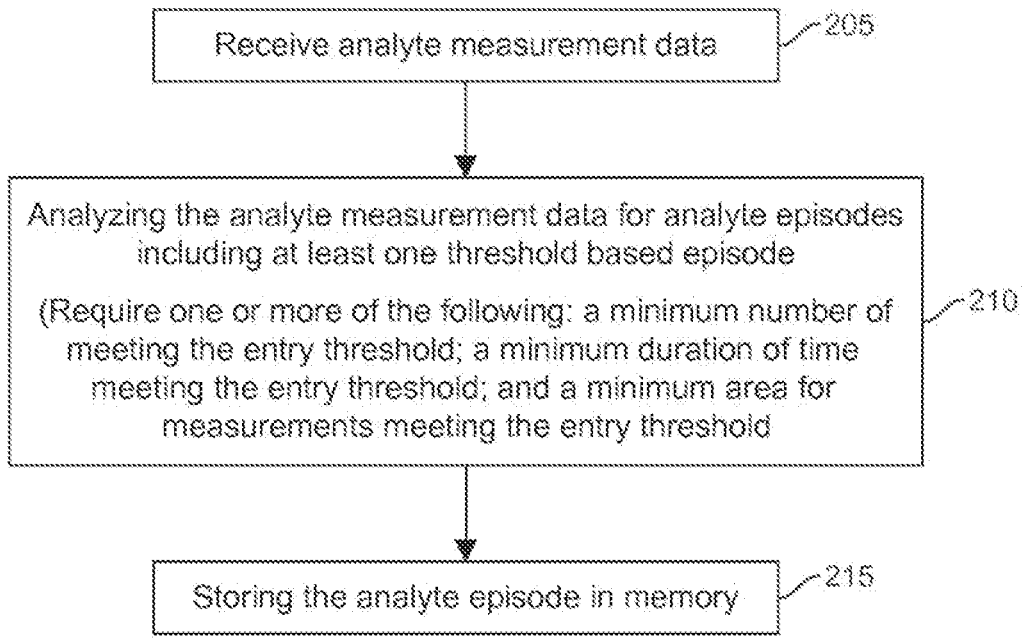
FIG. 2A illustrates a flowchart for a method of managing analyte measurement data, according to one embodiment.

FIG. 2A illustrates a flowchart for a method of managing analyte measurement data, according to one embodiment. As shown at block 205, analyte (e.g., glucose) measurement data is received by a data processing device, such as a glucose monitoring device, personal computer, a portable computer including a laptop or a handheld device (e.g., a personal digital assistant (PDA), a telephone including a cellular phone (e.g., a multimedia and Internet-enabled mobile phone including an iPhone™, a Blackberry®, or similar phone), etc. The analyte measurement data represents analyte measurements collected over a period of time.

Various time periods may be used, such as two weeks, one month, two months, or any other time period. For example, the time period may reflect the time between visits. The data processing device may receive the analyte measurement data from a glucose monitoring device or other device—e.g., another personal computer, portable computer, handheld device, or memory storage device, such as Flash memory stick, CD-ROM, etc.

At block 210, the analyte measurement data is analyzed for analyte episodes that are threshold based episodes. The threshold based episode is based on measurements meeting an entrance threshold for entering the episode. Furthermore, the threshold based episode requires at least one of: a minimum number of measurements meeting the entrance threshold; a minimum duration of time meeting the entrance threshold; and a minimum area for measurements meeting the entrance threshold. As later discussed and illustrated in FIG. 4, the area associated with the measurements meeting the entrance threshold is defined as the area on a glucose versus time plot of measurement that is between the measurements meeting the entrance threshold and the entrance threshold itself. At block 215, any threshold based episodes are stored in memory for further data management.

Figure 2B:
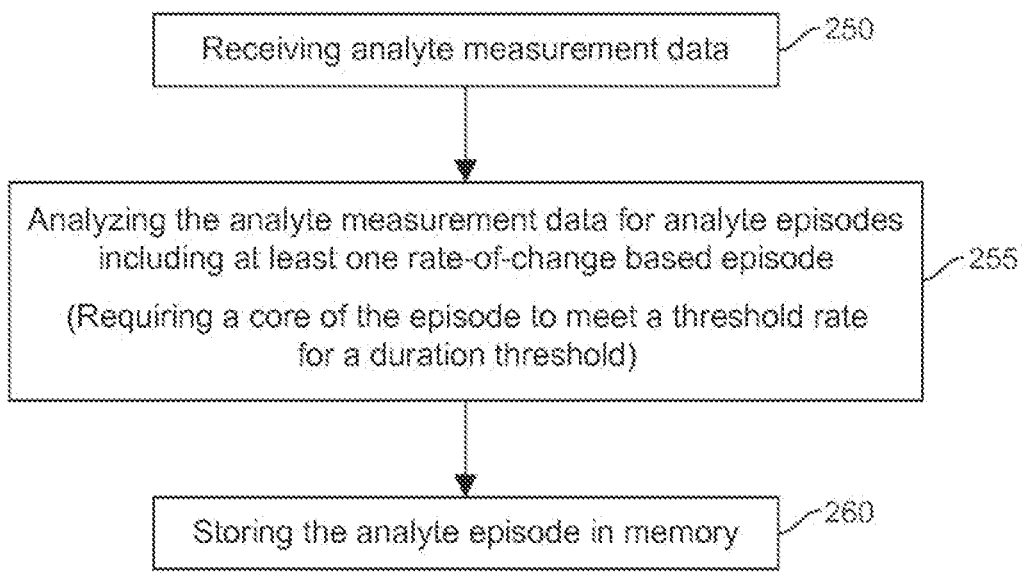
FIG. 2B illustrates a flowchart for a method of managing analyte measurement data, according to one embodiment.

FIG. 2B illustrates a flowchart of a method for managing analyte measurement data wherein the analyte measurement data is analyzed for analyte episodes that are rate of change based episodes. This is discussed in further detail later in the section for rate-of-change based episodes. In other embodiments, methods of managing analyte measurement data may include analyzing the measurement data for both threshold based episodes and rate-of-change based episodes.

Figure 3:
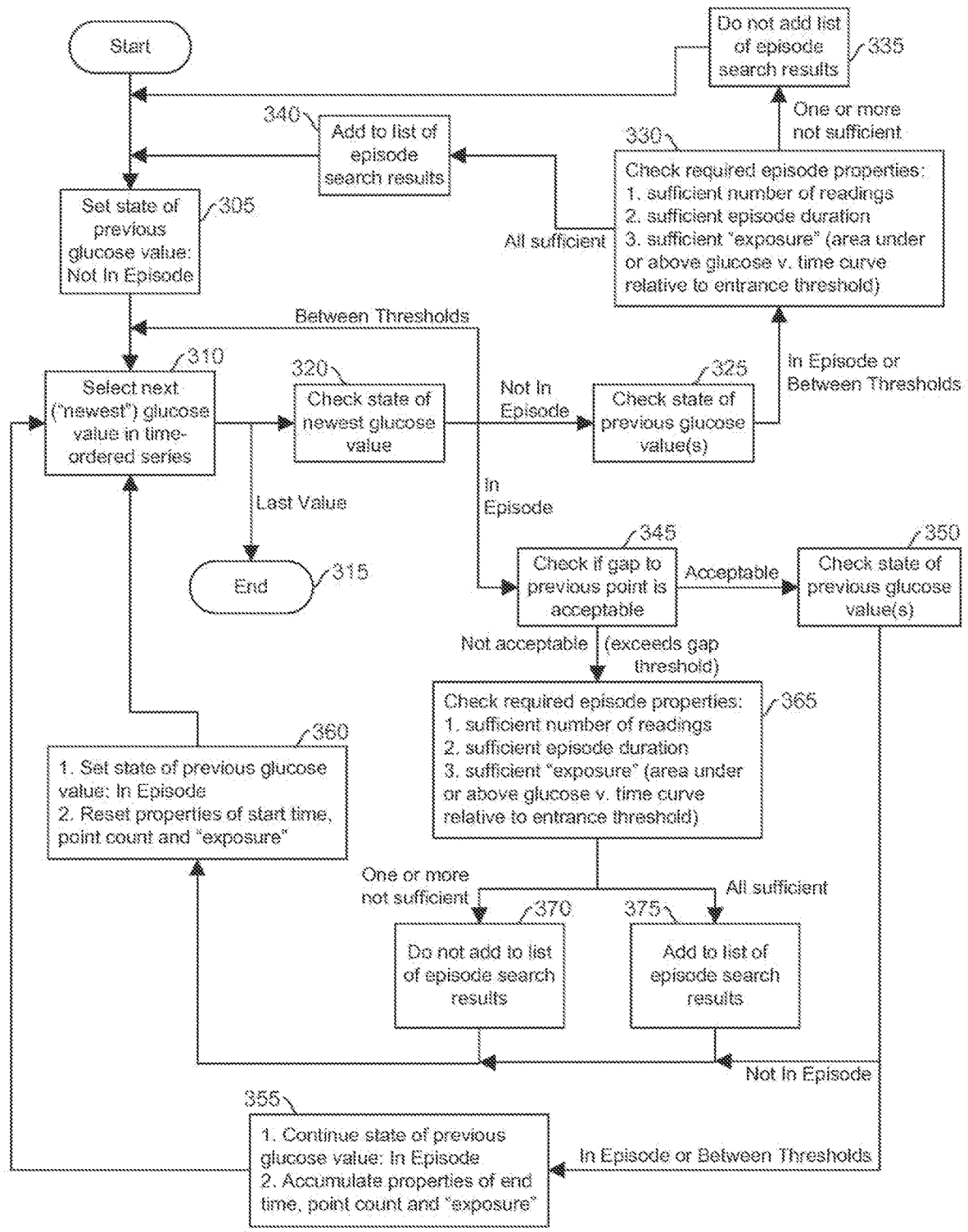
FIG. 3 illustrates a flowchart of a method for managing analyte (e.g., glucose) measurements that includes analyzing measurement data for threshold based episodes, according to one embodiment.

FIG. 3 illustrates a flowchart of a method for managing analyte (e.g., glucose) measurements that includes analyzing for threshold based episodes, according to one embodiment. The glucose measurement data is received and analyzed for threshold based episodes. The analysis may begin, for example, at the earliest measurement and continued through till the latest measurement.

Beginning at block 305, the previous glucose measurement value is set to "not in an episode" at the start of the analysis. At block 310, the "newest" or next glucose value (measurement) in time-ordered series is selected for analysis. If the next glucose value is the last value of the glucose measurement data, then the process is ended, as shown by block 315. If the next glucose value is not the last measurement, then the state of that glucose measurement is checked, as shown in block 320. If it is determined that the next glucose value is between thresholds, then the next glucose value in time-ordered series is selected at block 310. "Between episodes" refers to the being between the entrance threshold and exit threshold.

If it is determined that the measurement is not in episode, then the state of the previous glucose value is checked, as shown in block 325. Then it is determined if the previous measurements is in episode or between thresholds. For example, in the embodiment shown, at block 330, the episode requires: 1) minimum number of measurements meeting the entrance threshold; 2) a minimum duration of time meeting the entrance threshold; and 3) a minimum area for measurements meeting the entrance threshold (e.g., the area under or above the glucose v. time curve relative to entrance threshold for a hypoglycemic or hyperglycemic episode, respectively). Since all three criteria are required in this embodiment, if any one of the criteria is not met, then as shown at block 335, an episode does not exist and is not added to the search results (e.g., not stored in memory and used for further glucose measurement management). If all three criteria are met, as shown in block 340, then the episode exists and is added to the list of episodes (e.g., stored in memory and used for further glucose measurement management). The state of the previous glucose value is then set to "not in episode" so that episodes found in the subsequent data are analyzed independently of the previously identified episode.

Returning to block 320, if the next glucose value is determine to be in an episode, then the gap to the previous point is checked against a predetermined gap threshold, as shown in block 345. If the gap to the previous point is smaller than the gap threshold, then the state of the previous glucose value is checked, as shown in block 350. If it determined that the previous glucose value is in episode or between thresholds, then the state of the previous glucose value is continued in episode, as shown at block 355. Further at block 355, various properties, such as end time, point count and "exposure" or area are stored. Then a next glucose value in time-ordered series is selected, as shown at block 310. If it is determined at block 350 that the previous glucose value is not in episode, then the previous glucose value is set to in episode, and properties such as start time, point count and exposure (area) are stored, as shown in block 360. Then the next glucose value in time-ordered series is selected, as shown in block 310.

Returning to block 345, if the gap to the previous point meets the gap threshold (e.g., is larger than the gap threshold, or in other embodiments is equal to or larger), then it is determined at block 365 if the three criteria are met for the episode: 1) minimum number of measurements meeting the entrance threshold (e.g., minimum number of measurement readings after the entrance threshold was crossed); 2) a minimum duration of time meeting the entrance threshold; and 3) a minimum area for measurements meeting the entrance threshold (e.g., the area under or above the glucose v. time curve relative to entrance threshold). If any one of the criteria is not met, then as shown at block 370, the episode does not exist and is not added to the search results (e.g., stored in memory and used for further glucose measurement management). If all three criteria are met, as shown in block 375, then the episode exists and is added to the list of episodes (e.g., stored in memory and used for further glucose measurement management). The state of the previous glucose value is then set to "not in episode".

After blocks 370 and 375, the previous glucose value is set to in episode and the properties, such as start time, point count and exposure (area) are stored, as shown in block 360. Then the next glucose value in time-ordered series is selected, as shown in block 310.

Figure 4:
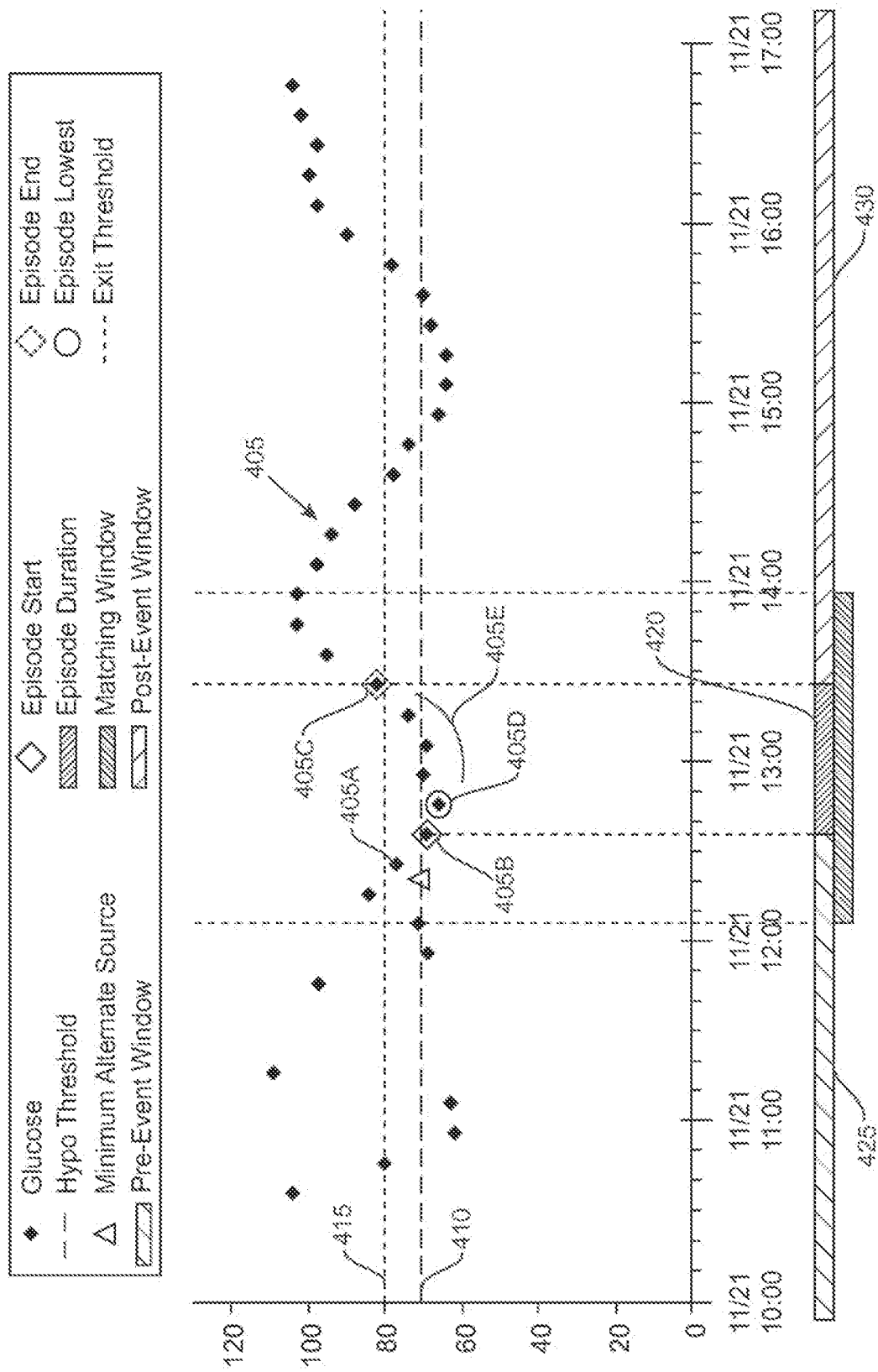
FIG. 4 illustrates a hypoglycemic episode for a set of glucose measurement data, according to one embodiment.

FIG. 4 illustrates a hypoglycemic episode for a set of glucose measurement data, according to one embodiment. As shown, glucose measurements 405 are plotted on a chart of glucose versus time. The entrance threshold 410 is shown for a hypoglycemia event. In this hypoglycemic example, the measurements that meet the entrance threshold are measurements that reach or exceed the entrance threshold by going below the entrance threshold (e.g., are smaller in value). As shown, measurement 405A is above the entrance threshold and thus not meeting the initial threshold for entering a hypoglycemic episode. Measurement 405B is the next measurement and "exceeds" the entrance threshold 410 for entering the hypoglycemic episode, and thus meets the entrance threshold. The next four measurements 405E are below the exit threshold 415. Measurement 405C is above the exit threshold 415 and thus "exceeds" and meets the exit threshold 415. In the embodiment shown, the three criteria are met for an episode: 1) minimum number of measurements outside the entrance threshold (e.g., the minimum number of measurements may be three measurements); 2) a minimum duration of time outside the entrance threshold (e.g., the minimum duration of time may be 20 minutes); and 3) a minimum area outside the entrance threshold (e.g., the area between the entrance threshold and the measurements that meet the entrance threshold).

Therefore, measurement 405B and 405C are the start and end of the episode, respectively, and the duration 420 of the episode spanning the time between the two. Therefore, the episode duration 420 is shown with the pre-event window 425 prior and post-event window 430 thereafter. Measurement 405D represents the lowest measurement in the episode.

Figure 5:
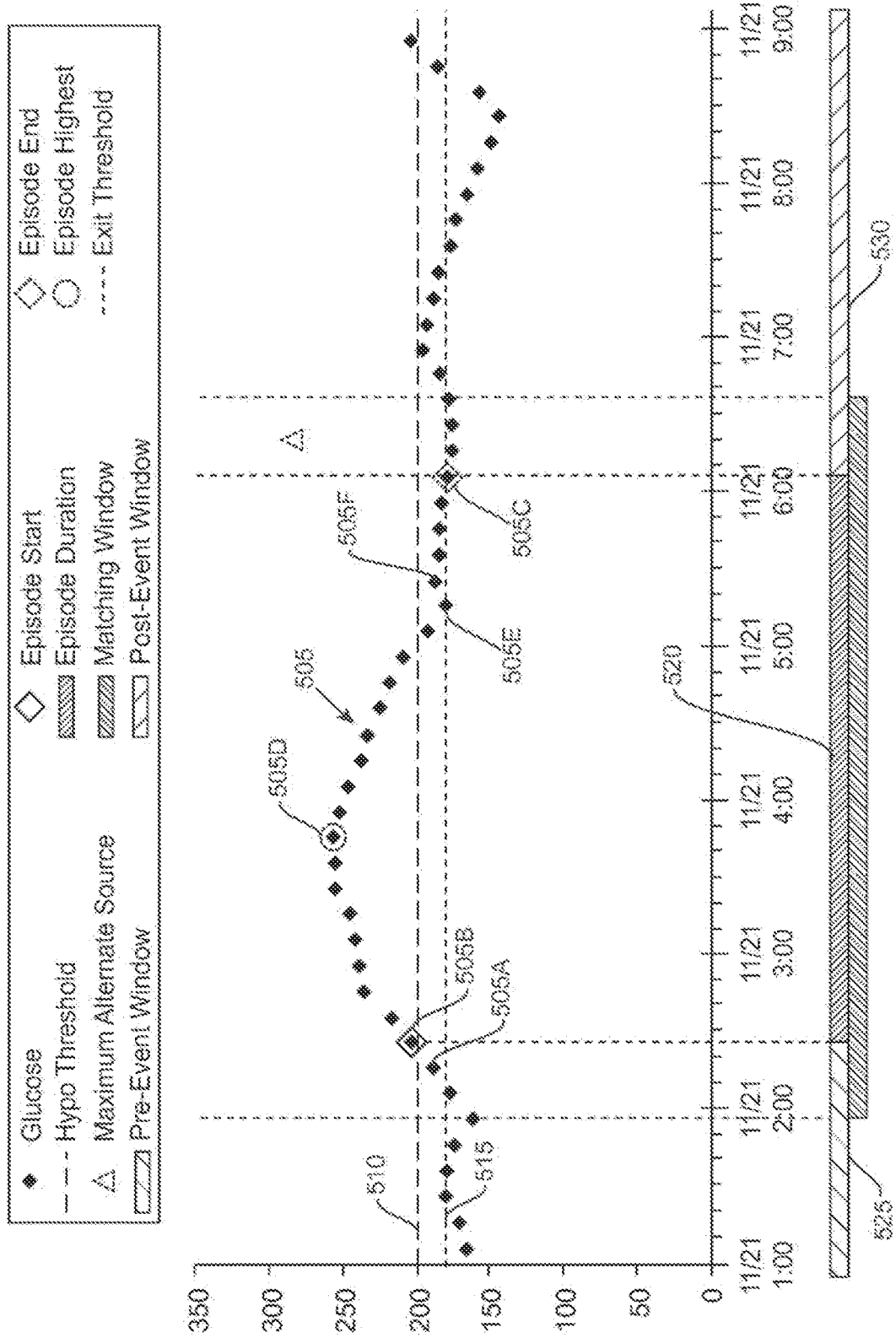
FIG. 5 illustrates a hyperglycemic episode for a set of glucose measurement data, according to one embodiment.

FIG. 5 illustrates a hyperglycemic episode for a set of glucose measurement data, according to one embodiment. As shown, glucose measurements 505 are plotted on a chart of glucose versus time. The entrance threshold 510 is shown for a hyperglycemia event. As shown, measurement 505A has not reached or exceeded (e.g., is below) the entrance threshold and thus not meeting the initial threshold requirement of entering a hyperglycemic episode. Measurement 505B is the next measurement and the entrance threshold 510 is met (e.g., reached or exceeded), and thus the first requirement of entering a hyperglycemic episode is met. Each consecutive measurement thereafter does not cross the exit threshold 515 until measurement 505E. However, the next measurement 505F returns back above the exit threshold and due to the duration threshold requirement, the measurements did not stay past the exit threshold for a required duration threshold (e.g., assuming an example duration threshold of 20 minutes). Thus the episode continues and does not end. Measurement 505C crosses the exit threshold and the next 3 measurements stay past the exit threshold (e.g., stay past the exit threshold for 30 minutes, which is longer than the example duration threshold of 20 minutes), thus meeting the duration threshold requirement. Therefore, the episode begins at measurement 505B and ends at measurement 505C.

The episode duration 520 is shown with the pre-event window 525 prior and post-event window 530 thereafter. The episode includes a maximum measurement 505D in the episode.

Rate-of-Change Based Episodes

As summarized above, in some aspects of the present disclosure, methods for managing analyte measurement data are provided. The methods include receiving analyte measurement data that represent data collected over a time period, and analyzing the analyte measurement data for analyte episodes within that time period. The analyte episodes include at least one rate-of-change based episode. The rate-of-change based episode requires a core of the episode to meet a threshold rate for a duration threshold. The methods also include storing the analyte episodes in memory. In some aspects of the present disclosure, articles of manufacture are provided that include a machine-readable medium having machine-executable instructions stored thereon for managing analyte measurement data according to the methods described above.

Grouping all consecutive monotonically increasing/decreasing points to form an episode creates issues and challenges in practical applications. For instance, small changes in magnitude may not be meaningful. Furthermore, signal variation may also present issues and problems by exaggerating the rate of change of very brief episodes. In one embodiment, the rate-of-change based episode requires a core of the episode to meet a threshold rate. The core is formed by two points having a threshold core rate-of-change for a duration threshold. Local extrema may then be scanned outward from the core to potentially define the episode.

Gaps in the measurement data can also significantly alter the episode durations. In one embodiment, a rate-of-change based episode is defined based on a gap threshold such that a single episode at any gaps shorter than the gap threshold, and split into two separate potential episodes at any gaps meeting the gap threshold. All of the points before the gap are considered a potentially complete episode with the last point being the point preceding the gap. All the points after the gap form the start of a potentially new episode. Again, the potential episodes are determined to be episodes if all other episode criteria are met.

Noise presents issues and problems by breaking the monotonicity of the change during periods of relatively slow change. In one embodiment, the rate-of-change based episode is defined based on a distance threshold between episodes such that two episodes within the distance threshold of each other are merged into a single episode. Thus, episodes that are close together are merged into a single episode, resulting in a newly defined episode containing all of the points between the first point of the first episode and the last point of the second episode.

In some instances, episodes merged in this way could have intermediate extreme points outside of the end values. In one embodiment, the single episode of the merger has intermediate extreme points outside of end values of the single episode, and wherein the single episode is then redefined beginning and ending at the intermediate extreme points. Episodes redefined in this way could include spikes caused by two closely spaced points where one of which is an outlier. The criteria requiring a duration threshold may be implemented in other embodiments to alleviate such issue.

Properties of change episodes, as so defined, can be defined, including but not limited to: maximum rate, delta (highest-lowest values), lowest value, and highest value. This provides a virtually limitless catalog of episode types, each of which, if independently clinically relevant, could form the basis for reports and analysis.

The following is an example pseudocode implementation of a rate-of-change based episode detection algorithm, according to one embodiment:

```
void Buildlist( )
{
  For Each FirstValue In Database
    For Each NextValue In Database (Starting at FirstValue)
      if (Distance between NextValue and point before it > MaxGap)
      {
        if (Last Episode passes checks)
        {
          //log last episode
        }
        FirstValue = NextValue
        Next FirstValue
      }
      else if (GetRateOfChange (FirstValue, NextValue) > Threshold)
      {
        StartingValue = ScanBackForLocalExtrema (FirstValue) ;
        EndingValue = ScanForwardFbrLpcalExtrema (NextValue) ;
        HighestValue = FindMaxBetween(StartingValue, EndingValue);
        LowestValue = FindMinBetween (StartingValue, EndingValue) ;
        StartingValue = (HighestValue or LowestValue);
        EndingValue = (LowestValue or HighestValue) ;
        if (StartingValue is close enough to EndingValue of last episode)
        {
          //merge with last episode
        }
        else
```

```
    {
        if (Last Episode passes checks)
        {
            //log last episode
        }
        //store this episode as last episode for next pass
    }
  }
  Next
NextValue
Next
FirstValue
```

As stated above, FIG. 2B illustrates a flowchart of a method for managing analyte (e.g., glucose) measurements that includes analyzing for rate-of-change based episodes. As shown at block 250, similar to block 205 in FIG. 2A, analyte (e.g., glucose) measurement data is received. At block 255, however, the analyte measurement data is analyzed for analyte episodes that are rate of change based episodes. The rate of change based episode requires a core of the episode to meet a threshold rate. The core is formed by two points having a threshold rate-of-change for a threshold duration of time (duration threshold). At block 260, any threshold based episodes are stored in memory for further data management.

Figure 6:
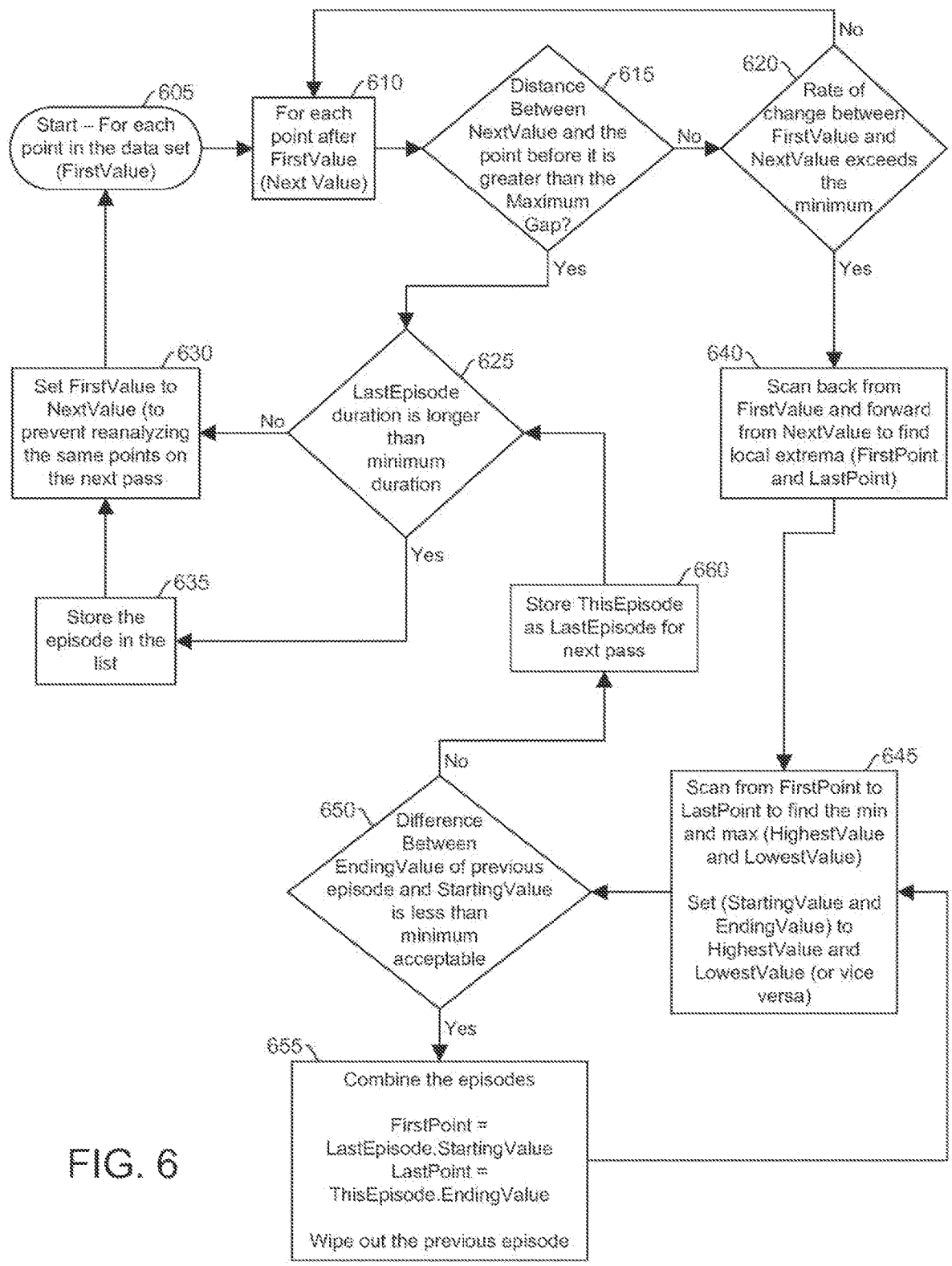
FIG. 6 illustrates a flowchart of a method for managing analyte (e.g., glucose) measurements that includes analyzing measurement data for rate-of-change based episodes, according to one embodiment.

FIG. 6 illustrates a flowchart of a method for managing analyte (e.g., glucose) measurements, according to one embodiment. The glucose measurement data is received and analyzed for rate-of-change based episodes. The analysis may begin, for example, at the earliest measurement and continued through till the latest measurement.

At block 605, for each point in the data set, a first value (measurement) is identified. At block 610, each point after the first value, referred to here as the next value, is identified and the distance between the next value and the first point is determined and compared to a gap threshold (e.g., a maximum gap), as shown in block 615. If the distance is not greater than the gap threshold, then it is determined if the rate of change between the first value and the next exceeds the minimum threshold rate, as represented at block 620. If it does not meet the threshold rate (e.g., does not exceed the threshold rate), then another 'next value' is selected (e.g., the next measurement in time-ordered series) for analysis, as shown by block 610.

If at block 615, the distance is greater than the gap threshold, then it is determined if the last episode is longer than a duration threshold, as shown by block 625. If it is not longer than the duration threshold, then the first value is set to the next value, to prevent reanalyzing the same points on the next pass, as represented by block 630 and arrow returning to block 605. If the last episode is longer than the duration threshold, then an episode is identified and stored in the episode list (e.g., in memory), as shown in block 635. Then the first value is set to the next value, to prevent reanalyzing the same points on the next pass, as represented by block 630 and arrow returning to block 605.

Returning to block 620, if the rate of change between the first value and the next value exceeds the minimum, then local extrema (e.g., first point and last point) are determined by scanning back form the first value and forward from the next value, as shown at block 640. Then the minimum and maximum (e.g., highest value and lowest value) are determined by scanning from the first point to the last point, as shown by block 645. The starting value and ending value are set to the highest value and the lowest value (or vice versa).

Then it is determined if the difference between the ending value of the previous episode and the starting value is less than a predetermined acceptable minimum (e.g., a distance threshold between the two episodes). If so, then the two episodes are combined, as shown by block 655. The first point is equal to the starting value of the last episode, and the last point is the ending value of this episode. The previous episode is eliminated. Then to block 645, where the minimum and maximum (e.g., highest value and lowest value) are determined by scanning from the first point to the last point. The starting value and ending value are set to the highest value and the lowest value (or vice versa).

If at block 650, the difference between the ending value of the previous episode and the starting value is not less than a predetermined acceptable minimum, then this episode is stored as the last episode for the next pass, as shown by block 660. Then again back to block 625 where it is determined if the last episode is longer than a duration threshold.

Figure 7:
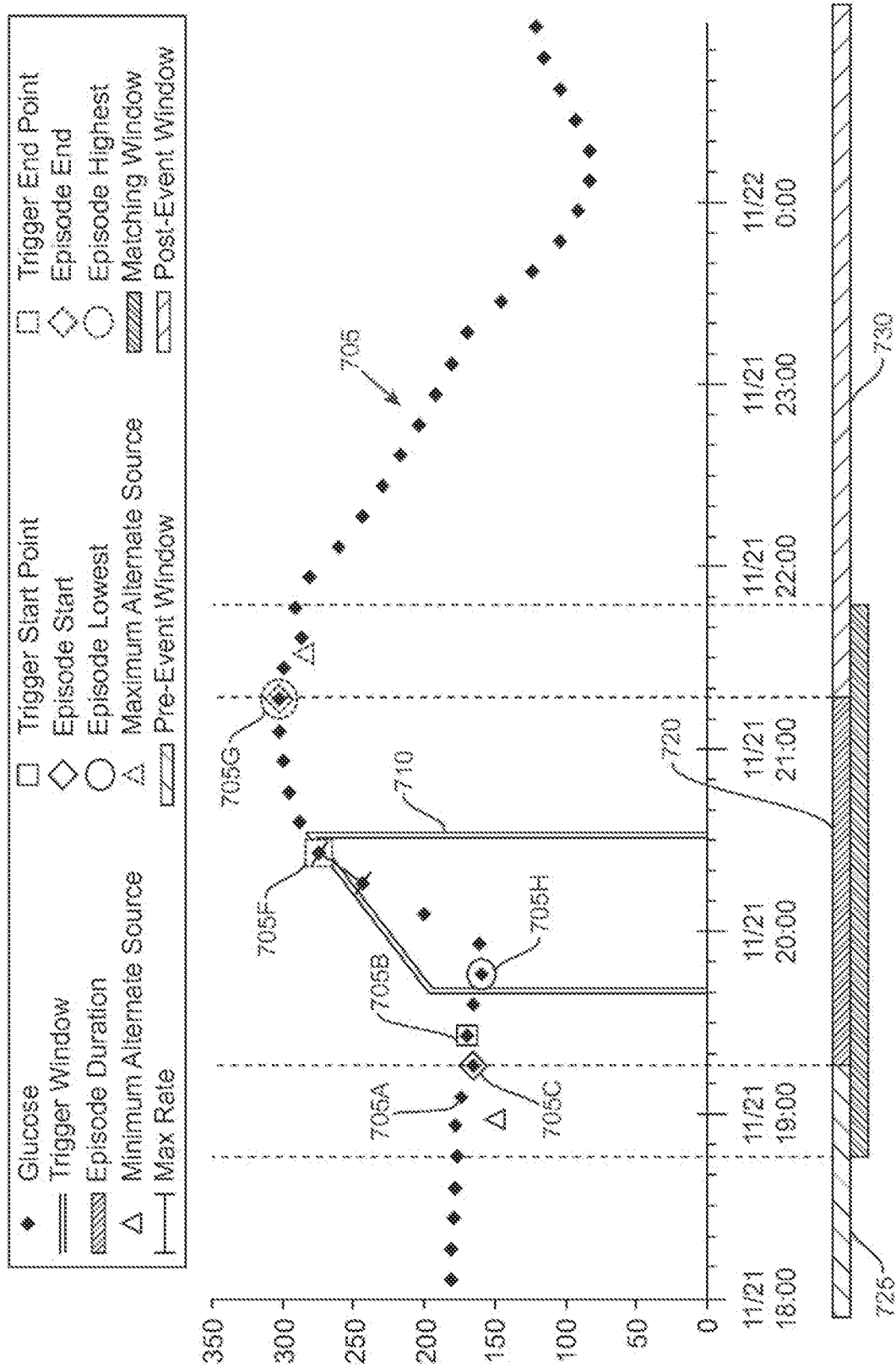
FIG. 7 illustrates an example of a detection of a glucose rise episode in a set of glucose measurement data, according to one embodiment.

FIG. 7 illustrates an example of a detection of a glucose rise episode in a set of glucose measurement data, according to one embodiment. As shown glucose measurement data 705 is plotted on a chart of glucose versus time. Starting with the earliest measurements on the left, each measurement is compared with future measurements to determine if a predetermined rate threshold is met (e.g., reached or exceeded). For example, in the example shown, measurement 705A and prior measurements to the left, do not have any future measurements that create a rate-of-change above a predetermined threshold rate. However, measurement 705B and future measurement 705F embody a rate-of-change above the predetermined threshold rate. For example, the top of trigger window 710 represents the predetermined threshold rate and is shown for measurement 705B. As shown, measurement 705F is above the top of trigger window 710, and thus possesses a rate-of-change greater than the predetermined rate threshold of the trigger window 710. A core is thus defined from measurement 705B as the trigger start point to measurement 705F as the trigger end point. Note that for all the measurements prior to measurement 705B, no future measurements exist that would fall above the top of similarly drawn trigger windows (not shown) which align with the corresponding measurement being analyzed.

Local extrema are then scanned for outside the core. For example, scanning from measurement 705B to the left, a minimum point is scanned for. Measurement 705C is determined to be the minimum and thus the episode start point. Similarly, scanning from measurement 705F to the right, a maximum point is scanned for. Measurement 705G is determined to be the maximum and thus the episode end point. Note that the episode includes a minimum and maximum point for the episode itself, which may or may not be the same as the local extrema searched for. In this case, the minimum measurement 705H is the episode's minimum while measurement 705G is the episode's maximum. The episode duration 720 is shown with the pre-event window 725 prior and post-event window 730 thereafter. The process may then be repeated for later measurements past the episode to find additional rate-of-change based episodes within the measurement data.

Figure 8:
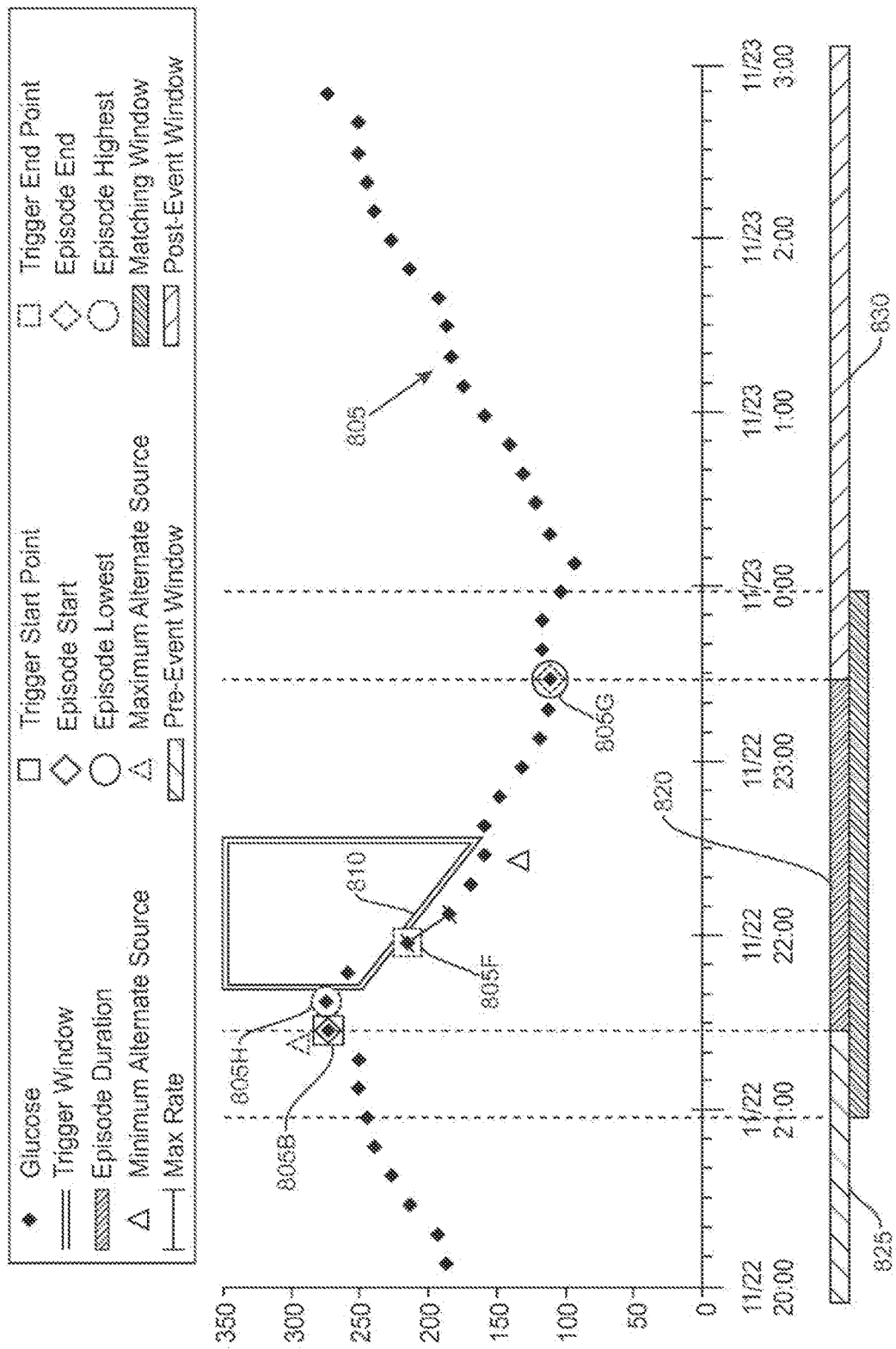
FIG. 8 illustrates an example of a detection of a glucose fall episode in a set of glucose measurement data, according to one embodiment.

FIG. 8 illustrates an example of a detection of a glucose fall episode in a set of glucose measurement data, according to one embodiment. As shown glucose measurement data 805 is plotted on a chart of glucose versus time. Starting with the earliest measurements on the left, each measurement is compared with future measurements to determine if a predetermined rate threshold is met (e.g., reached or exceeded).

For example, in the example shown, measurement 805A and prior measurements to the left, do not have any future measurements that create a rate-of-change above a predetermined threshold rate. However, measurement 805B and future measurement 805F possess a rate-of-change exceeding the predetermined threshold rate. For example, the bottom of trigger window 810 represents the predetermined threshold rate and is shown for measurement 805B. As shown, measurement 805F is below the bottom of trigger window 810, and thus possesses a rate-of-change exceeding than the predetermined rate threshold of the trigger window 810. A core is thus defined from measurement 805B as the trigger start point to measurement 805F as the trigger end point. Note that for all the measurements prior to measurement 805B, no future measurements exist that would fall below the bottom of similarly drawn trigger windows (not shown) which align with the corresponding measurement being analyzed.

Local extrema are then scanned for outside the core. For example, scanning from measurement 805B to the left, a maximum point is scanned for. Measurement 805B is determined to be the minimum and thus the episode start point. Similarly, scanning from measurement 805F to the right, a minimum point is scanned for. Measurement 805G is determined to be the minimum and thus the episode end point. Note that the episode includes a minimum and maximum point for the episode itself, which may or may not be the same as the local extrema searched for. In this case, the minimum measurement 805G is the episode's minimum while measurement 805H is the episode's maximum. The episode duration 820 is shown with the pre-event window 825 prior and post-event window 830 thereafter. The process may then be repeated for later measurements past the episode to find additional rate-of-change based episodes within the measurement data.

Devices and Systems

Figure 9:
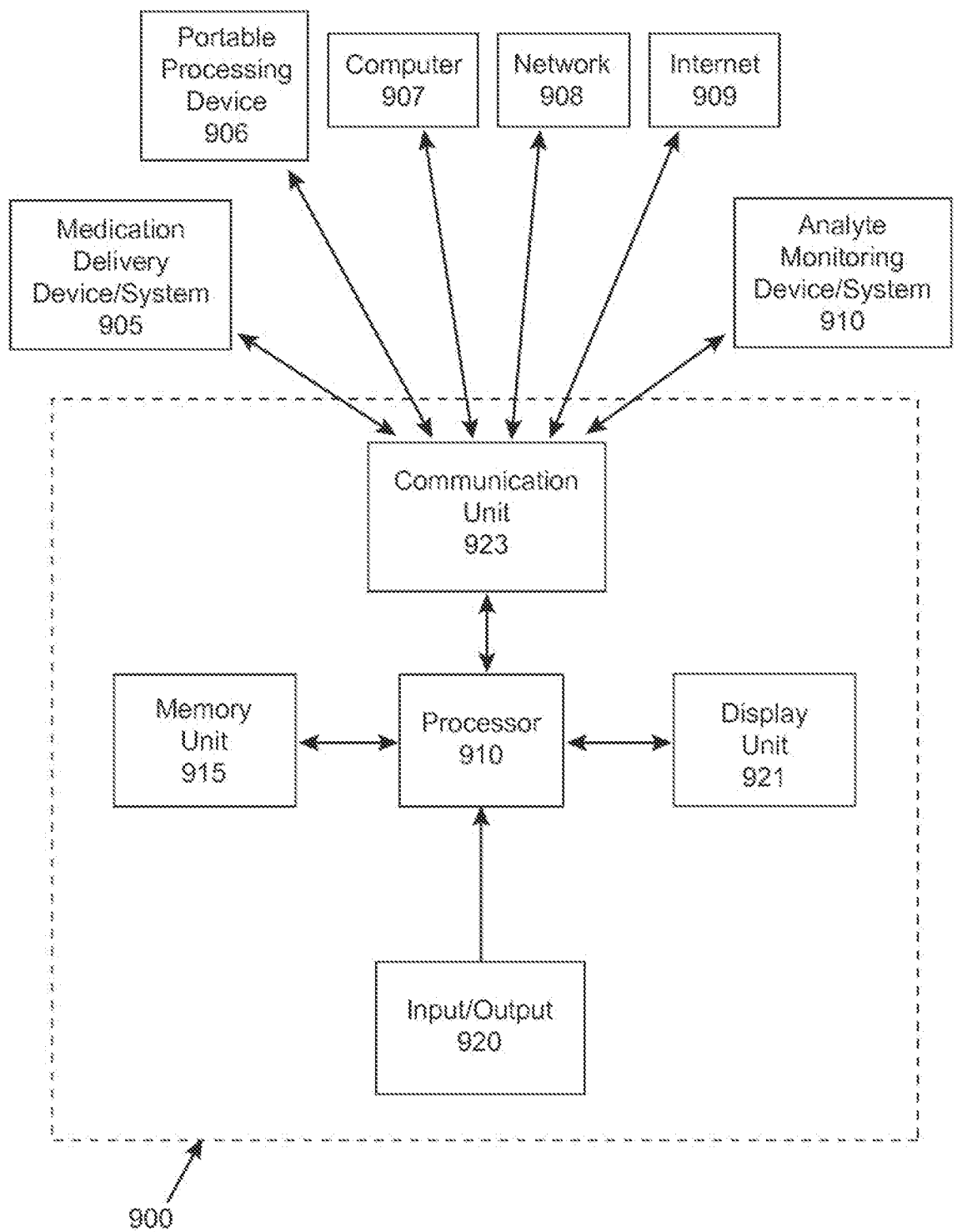
FIG. 9 illustrates a data processing device that may perform the methods described herein, according to one embodiment.
Figure 10:
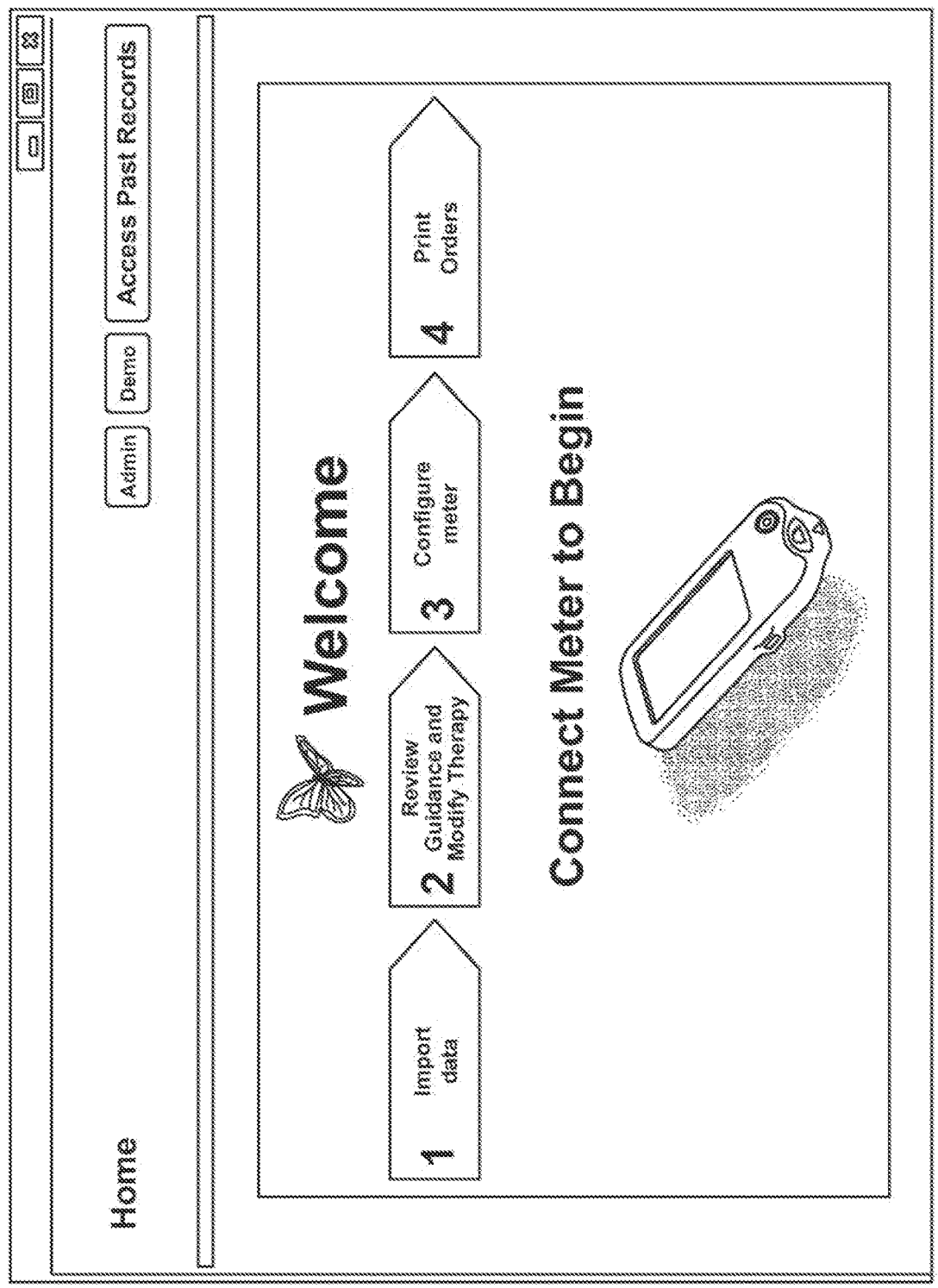
Figure 11:
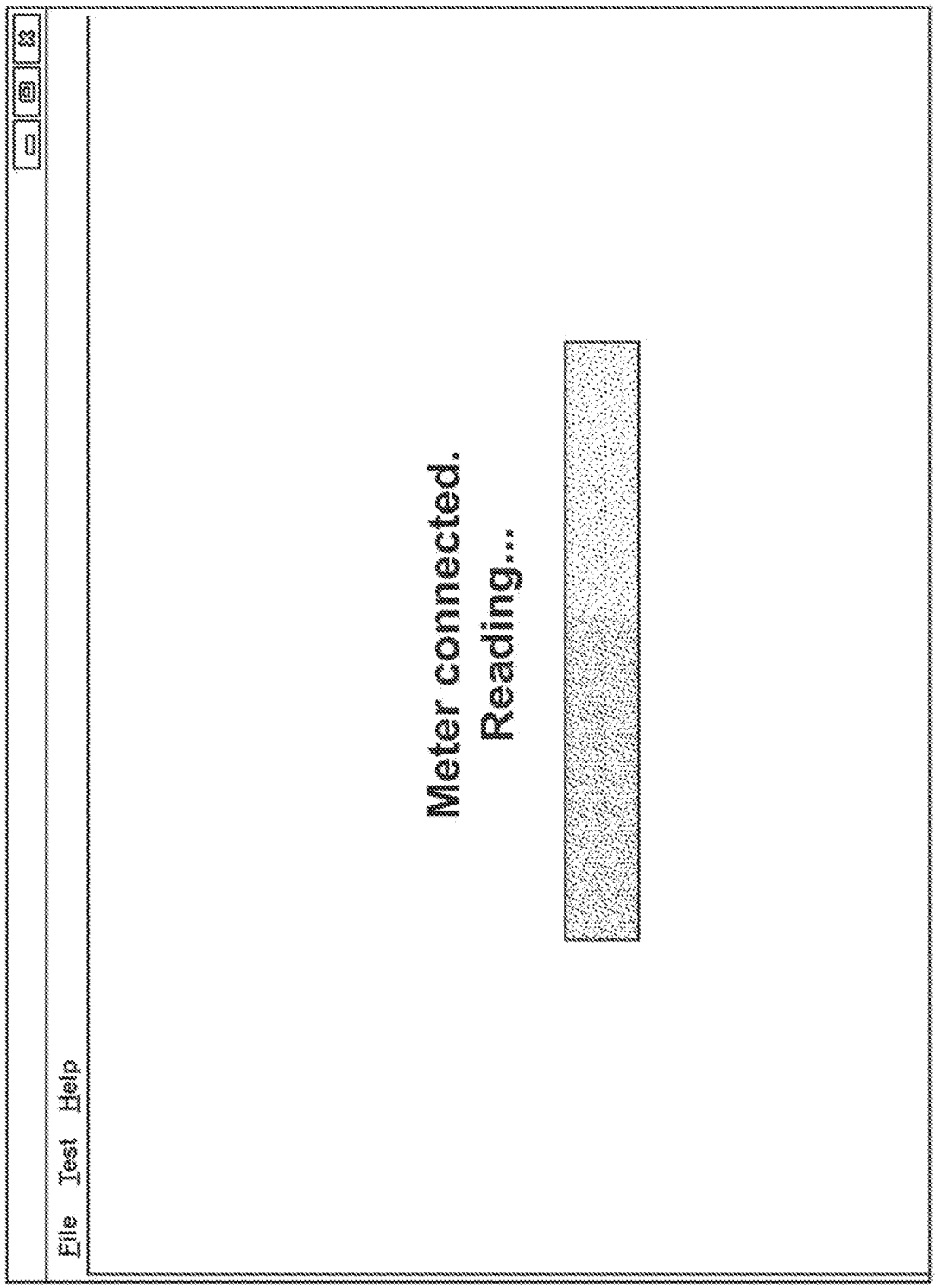

FIG. 9 illustrates a data processing device that may perform the methods described herein, according to one embodiment. The data processing device 900 is shown including processor 910, communication unit 923, memory 915, display unit 921 and input/output 920. The data processing device may communicate, either wired or wireless, with other devices, such as a medication delivery device 905, portable processing device 906, computer 907, or an analyte monitoring device 910. The data processing device may also be coupled to networks 908 and/or the internet 909. The analyte monitoring device and/or system 910 may, for example, provide for discrete monitoring of one or more analytes using an in vitro blood glucose ("BG") meter and an analyte test strip. In other embodiments, the glucose monitoring device may provide for continuous, periodic, and/or intermittent in vivo monitoring of the level of one or more analytes. For instance, such a system may include, for example, an analyte sensor at least a portion of which is to be positioned beneath a skin surface of a user for a period of time.

In one embodiment, data processing device 900 may be a computer of a physician or HCP that connects to glucose monitoring device 910 of a patient. The computer 900 may then communicate data to and from other computers 907 and the internet 909. In another embodiment, the data processing device 900 may be a handheld device, such as a cellular phone or hand-held computer, that connects with the glucose monitoring device 910 of a patient. The device 900 may then communicate data to and from a personal computers 907, for example, via a direct wired or wireless connection, or via the internet 909.

In one embodiment, instructions for performing the methods described herein may be stored in memory unit 915 and executed by processor 910. The communication unit 923 may be used to establish a communication link between the analyte monitoring device 910 and the data processing device 900. Display unit 921 and input/output 920 may be used to provide the user interface and receive user input. Input/output 920 may also be used to connect to a printer to print reports.

Each of the various references, presentations, publications, provisional and/or non-provisional U.S. patent applications, U.S. patents, non-U.S. patent applications, and/or non-U.S. patents that have been identified herein, is incorporated herein by reference in its entirety.

Other embodiments and modifications within the scope of the present disclosure will be apparent to those skilled in the relevant art. Various modifications, processes, as well as numerous structures to which the embodiments of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example. Although various aspects and features of the present disclosure may have been described largely with respect to applications, or more specifically, medical applications, involving diabetic humans, it will be understood that such aspects and features also relate to any of a variety of applications involving non-diabetic humans and any and all other animals. Further, although various aspects and features of the present disclosure may have been described largely with respect to applications involving partially implanted sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the present disclosure have been described with respect to various embodiments and specific examples herein, all of which may be made or carried out conventionally, it will be understood that the invention is entitled to protection within the full scope of the appended claims.

It should be understood that techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

What is claimed is:

1. A system comprising:
    an input configured to receive analyte measurement data of a sensor, the analyte measurement data representing analyte measurement data collected over a time period;
    one or more processors coupled with the input and a memory storing instructions, wherein the instructions, when executed by the one or more processors, cause the one or more processors to:
        analyze the analyte measurement data for potential analyte episodes within the time period, wherein the potential analyte episodes comprise at least one potential rate-of-change based episode, wherein each of the at least one potential rate-of-change based episodes comprises a rate of change of an analyte value over time, and wherein each of the at least one potential rate-of-change based episodes includes two points having a rate-of-change above a threshold rate-of-change for a duration threshold;
        determine if an episode of the at least one potential rate-of-change based episode includes a gap in analyte measurement data;
        split the episode of the at least one potential rate-of-change based episode that includes the gap in analyte measurement data into first and second potential episodes if the gap in analyte measurement data is larger than a gap threshold;
        determine that the first potential episode is a first rate-of-change based episode if the first potential episode includes a first set of two points having a rate-of-change above the threshold rate-of-change for the duration threshold;
        determine that the second potential episode is a second rate-of-change based episode if the second potential episode includes a second set of two points having a rate-of-change above the threshold rate-of-change for the duration threshold; and
        store the first and second rate-of-change based episodes in a memory.

2. The system of claim 1, wherein the instructions further cause the one or more processors to establish a communication link with a sensor control device, wherein the analyte measurement data is received via the communication link.

3. The system of claim 1, wherein the analyte is glucose.

4. The system of claim 1, wherein the analyte is a ketone body.

5. A computer-implemented method for analyte monitoring management, comprising:
    receiving analyte measurement data, the analyte measurement data representing analyte measurement data collected over a time period;
    analyzing the analyte measurement data for potential analyte episodes within the time period;
        wherein the potential analyte episodes comprise at least one potential rate-of-change based episode, the potential rate of change being the rate of change of the analyte value over time;
        wherein the at least one potential rate-of-change based episode extends between two points having a rate-of-change above a threshold rate-of-change for a duration threshold;
    determining if an episode of the at least one potential rate-of-change based episode includes a gap in analyte measurement data;
    splitting the episode of the at least one potential rate-of-change based episode that includes the gap in analyte measurement data into first and second potential episodes when the gap in analyte measurement data is greater than a gap threshold;
    determining that the first potential episode is a first rate-of-change based episode if the first potential episode includes a first set of two points having a rate-of-change above the threshold rate-of-change for the duration threshold;
    determining that the second potential episode is a second rate-of-change based episode if the second potential episode includes a second set of two points having a rate-of-change above the threshold rate-of-change for the duration threshold; and
    storing the first and second rate-of-change based episodes in a memory.

6. The method of claim 5, further comprising the step of establishing a communication link with an analyte monitoring device.

7. The method of claim 6, wherein the analyte measurement data is received via the communication link.

8. The method of claim 5, wherein the analyte is glucose.

9. The method of claim 5, wherein the analyte is a ketone body.

* * * * *